(12) United States Patent
Parihar et al.

(10) Patent No.: US 9,867,600 B2
(45) Date of Patent: Jan. 16, 2018

(54) METHOD OF FITTING POUCH IN TISSUE RETRIEVAL DEVICE

(71) Applicant: Ethicon Endo-Surgery, Inc., Cincinnati, OH (US)

(72) Inventors: Shailendra K. Parihar, Mason, OH (US); Atul M. Godbole, Liberty Township, OH (US); Wells D. Haberstich, Loveland, OH (US); Frederick E. Shelton, IV, Hillsboro, OH (US); Gregory W. Johnson, Milford, OH (US)

(73) Assignee: Ethicon LLC, Guaynabo, PR (US)

( * ) Notice: Subject to any disclaimer, the term of this patent is extended or adjusted under 35 U.S.C. 154(b) by 273 days.

(21) Appl. No.: 14/611,387

(22) Filed: Feb. 2, 2015

(65) Prior Publication Data
US 2015/0209020 A1 Jul. 30, 2015

Related U.S. Application Data

(62) Division of application No. 12/693,491, filed on Jan. 26, 2010, now Pat. No. 8,986,321.

(51) Int. Cl.
*A61B 17/00* (2006.01)
*A61B 90/00* (2016.01)
*A61B 50/00* (2016.01)

(52) U.S. Cl.
CPC ............ *A61B 17/00234* (2013.01); *A61B 2017/00004* (2013.01); *A61B 2017/00287* (2013.01);

(Continued)

(58) Field of Classification Search
CPC ........ A61B 2017/00287; A61B 17/221; A61B 2017/2212; A61B 2017/00358; A61B 17/32056
See application file for complete search history.

(56) References Cited

U.S. PATENT DOCUMENTS 5,147,371 A   9/1992   Washington et al.
5,465,731 A   11/1995  Bell et al.
(Continued)

FOREIGN PATENT DOCUMENTS

EP   0 947 166       10/1999
WO   WO 2005/112783  12/2005

OTHER PUBLICATIONS

International Search Report and Written Opinion dated May 25, 2011 for Application No. PCT/US2011/021047.

*Primary Examiner* — Thomas McEvoy
(74) *Attorney, Agent, or Firm* — Frost Brown Todd LLC

(57) ABSTRACT

A tissue retrieval device includes a tubular member, an expandable member, and a tissue retrieval bag. The introducer tube is sized to be inserted into a patient through a trocar. The bag may be selectively opened by the expandable member within the patient. The bag may receive a tissue specimen and be withdrawn from the patient. The bag may be manipulated for packing within the tubular member in a variety of ways. Manipulation of the bag may include folding the bag about axes that are perpendicular to or parallel to the tubular member; rolling the bag about axes that are perpendicular to or parallel to the tubular member; or wrapping the bag about the expandable member, wrapping the bag about a rod, or twisting the bag at a position distal to the expandable member. The tubular member may comprise an environmentally responsive capsule.

20 Claims, 17 Drawing Sheets

(52) U.S. Cl.
CPC ............... *A61B 2017/00398* (2013.01); *A61B 2050/002* (2016.02); *A61B 2090/037* (2016.02)

(56) References Cited

U.S. PATENT DOCUMENTS

| | | |
|---|---|---|
| 5,480,404 A | 1/1996 | Kammerer et al. |
| 5,647,372 A | 7/1997 | Tovey et al. |
| 5,681,324 A | 10/1997 | Kammerer et al. |
| 5,971,995 A | 10/1999 | Rousseau |
| 6,409,733 B1 | 6/2002 | Conlon et al. |
| 7,044,956 B2 | 5/2006 | Vetter et al. |
| 7,762,959 B2 | 7/2010 | Bilsbury |
| 8,016,771 B2 | 9/2011 | Orban, III |
| 8,409,216 B2 | 4/2013 | Parihar et al. |
| 8,409,217 B2 | 4/2013 | Parihar et al. |
| 8,414,596 B2 | 4/2013 | Parihar et al. |
| 8,419,217 B2 | 4/2013 | Lu et al. |
| 8,419,749 B2 | 4/2013 | Shelton, IV et al. |
| 8,425,533 B2 | 4/2013 | Parihar et al. |
| 8,444,655 B2 | 5/2013 | Parihar et al. |
| 8,986,321 B2 | 3/2015 | Parihar et al. |
| 2011/0184311 A1 | 7/2011 | Parihar et al. |

FIG. 25
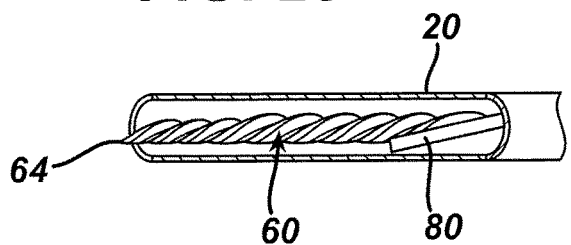
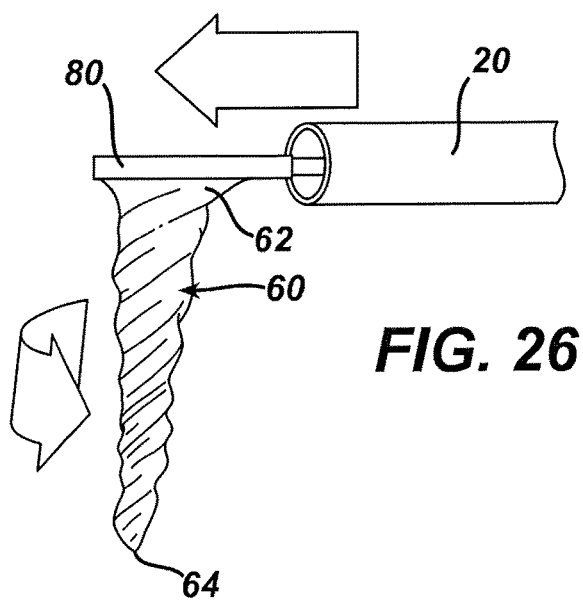
FIG. 26
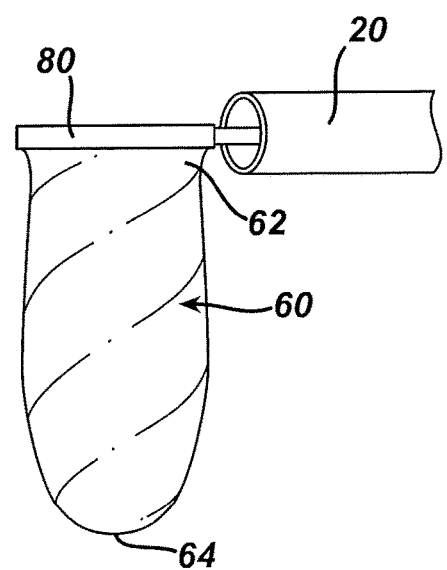
FIG. 27

FIG. 28
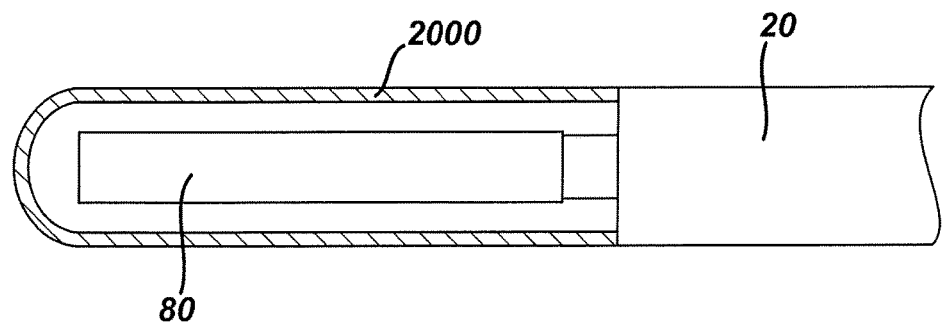
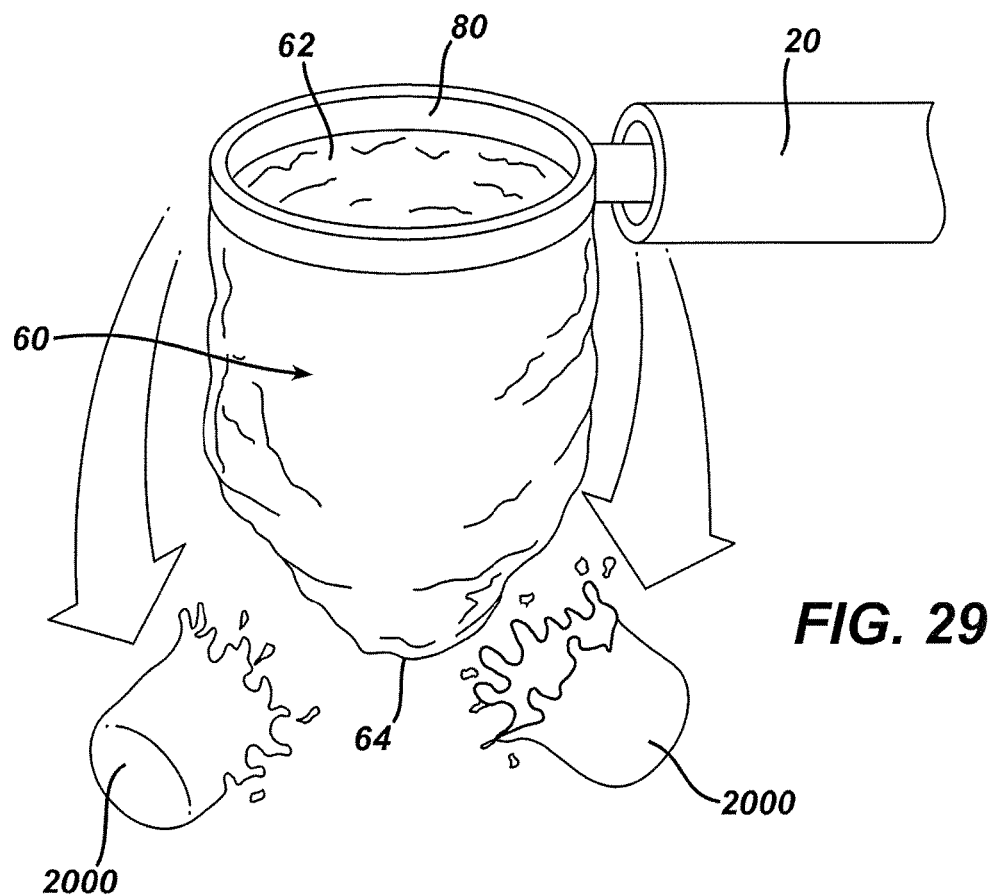
FIG. 29

METHOD OF FITTING POUCH IN TISSUE RETRIEVAL DEVICE

This application is a divisional of U.S. patent application Ser. No. 12/693,491, entitled "Method of Fitting Pouch in Tissue Retrieval Device," filed Jan. 26, 2010, now U.S. Pat. No. 8,986,321, issued on Mar. 24, 2015.

BACKGROUND

Endoscopic surgery (e.g., laparoscopy) is a procedure wherein surgery is performed through a series of small openings or incisions in a patient. This type of surgery may reduce or eliminate the need for large incisions and may change some otherwise open surgical procedures such as gall bladder removal to simple outpatient surgery. Consequently, the patient's recovery time may change from weeks to days. These types of surgeries may be used for repairing defects or for the removal of diseased tissue or organs from areas of the body such as the abdominal cavity. In some of these procedures, biological material or tissue may be removed or excised from the body through a small opening such as an incision, a small natural orifice, or through a small diameter laparoscopic access port such as a trocar.

Various types of tissue retrieval pouches or bags have been developed to allow for the removal of tissue through a small opening, orifice, or port in an endoscopic surgical procedure. Various instruments have also been devised for introducing, opening, positioning, and closing tissue retrieval bags within a patient; and for removing the bags and enclosed tissue from the surgical site. Some exemplary retrieval bags and associated instruments are disclosed in U.S. Pat. No. 5,465,731, entitled "Specimen Retrieval Pouch and Method for Use," issued Nov. 14, 1995, the disclosure of which is incorporated by reference herein; U.S. Pat. No. 5,480,404, entitled "Surgical Tissue Retrieval Instrument," issued Jan. 2, 1996, the disclosure of which is incorporated by reference herein; U.S. Pat. No. 5,647,372, entitled "Specimen Retrieval Pouch and Method for Use," issued Jul. 15, 1997, the disclosure of which is incorporated by reference herein; U.S. Pat. No. 5,971,995, entitled "Surgical Pouch Instrument," issued Oct. 26, 1999, the disclosure of which is incorporated by reference herein; and U.S. Pat. No. 6,409,733, entitled "Specimen Retrieval Bag," issued Jun. 25, 2002, the disclosure of which is incorporated by reference herein.

While a variety of tissue retrieval devices have been made and used, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings. In the drawings, like numerals represent like elements throughout the several views.

FIG. 25 is a side view of the distal end of an exemplary tissue retrieval device, with a retrieval bag in an exemplary twisted configuration and in a retracted position, and with part of an introducer tube shown in cross-section.

FIG. 26 is a side view of the tissue retrieval device of FIG. 25, with the retrieval bag in a deployed position and with the retrieval bag untwisting from the twisted configuration of FIG. 25.

FIG. 27 is a side view of the tissue retrieval device of FIG. 25, with the retrieval bag in the deployed position and with the retrieval bag untwisted.

FIG. 28 is a side view of the distal end of an exemplary tissue retrieval device, with a resilient hoop contained within a capsule, with the capsule shown in cross section, and with a retrieval bag omitted.

FIG. 29 is a side view of the tissue retrieval device of FIG. 28, with the capsule dissolving from the tissue retrieval device to reveal the resilient hoop and retrieval bag.

Figure 1:
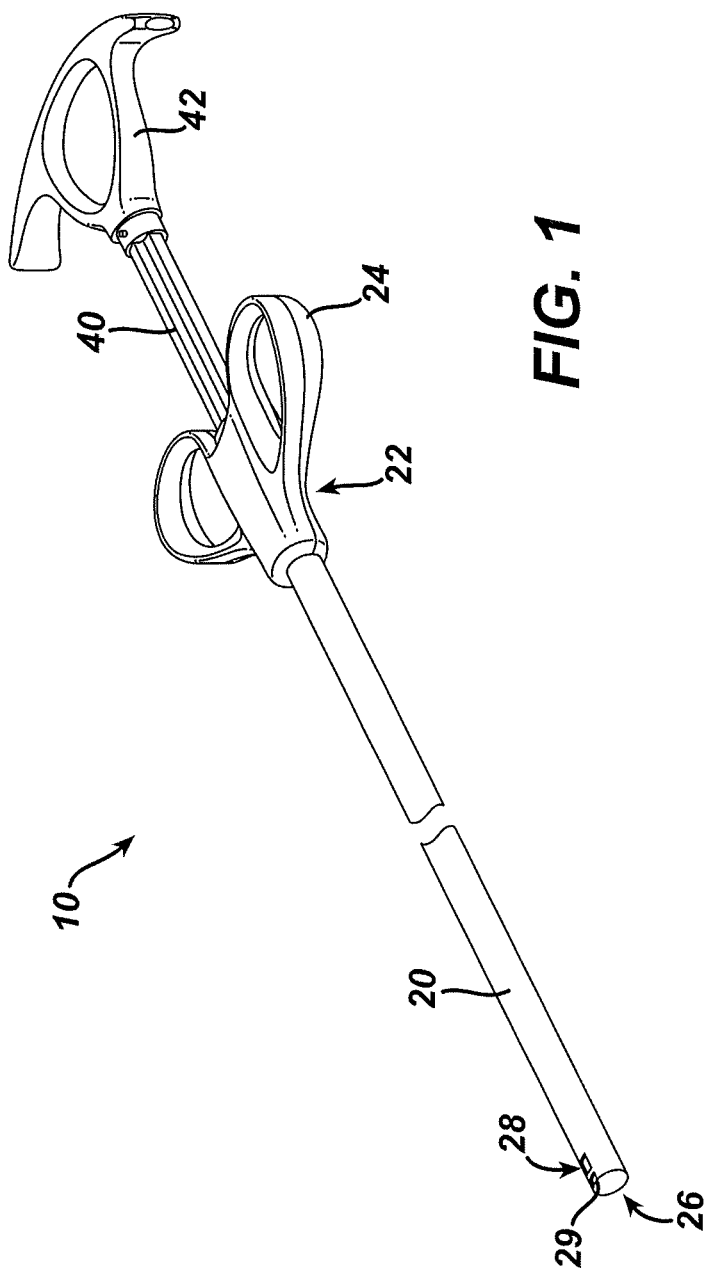
FIG. 1 is a perspective view of an exemplary tissue retrieval device, with a retrieval bag in a retracted position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples should not be used to limit the scope of the present invention. Other features, aspects, and advantages of the versions disclosed herein will become apparent to those skilled in the art from the following description, which is by way of illustration, one of the best modes contemplated for carrying out the invention. As will be realized, the versions described herein are capable of other different and obvious aspects, all without departing from the invention. Accordingly, the drawings and descriptions should be regarded as illustrative in nature and not restrictive.

I. Exemplary Tissue Retrieval Devices

A. Exemplary Tissue Retrieval Device with Translatable Rod

Figure 2:
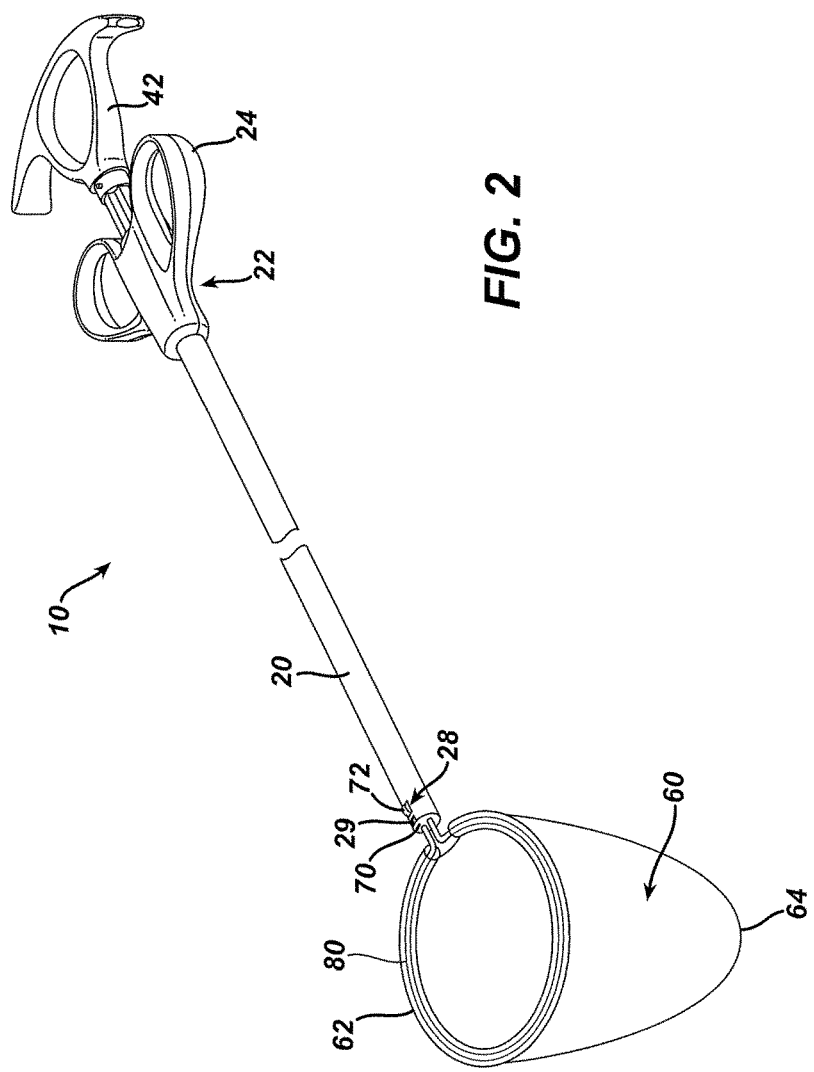
FIG. 2 is a perspective view of the tissue retrieval device of FIG. 1, with the retrieval bag in a deployed position.
Figure 3:
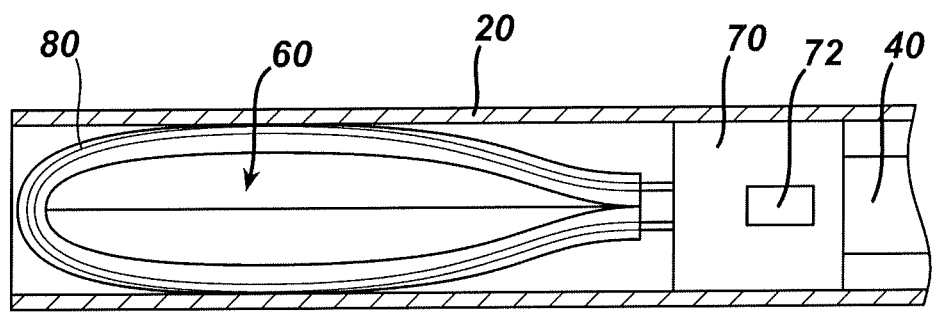
FIG. 3 is a top view of the distal end of the tissue retrieval device of FIG. 1, with the retrieval bag in the retracted position and with the introducer tube shown in cross section.
Figure 4:
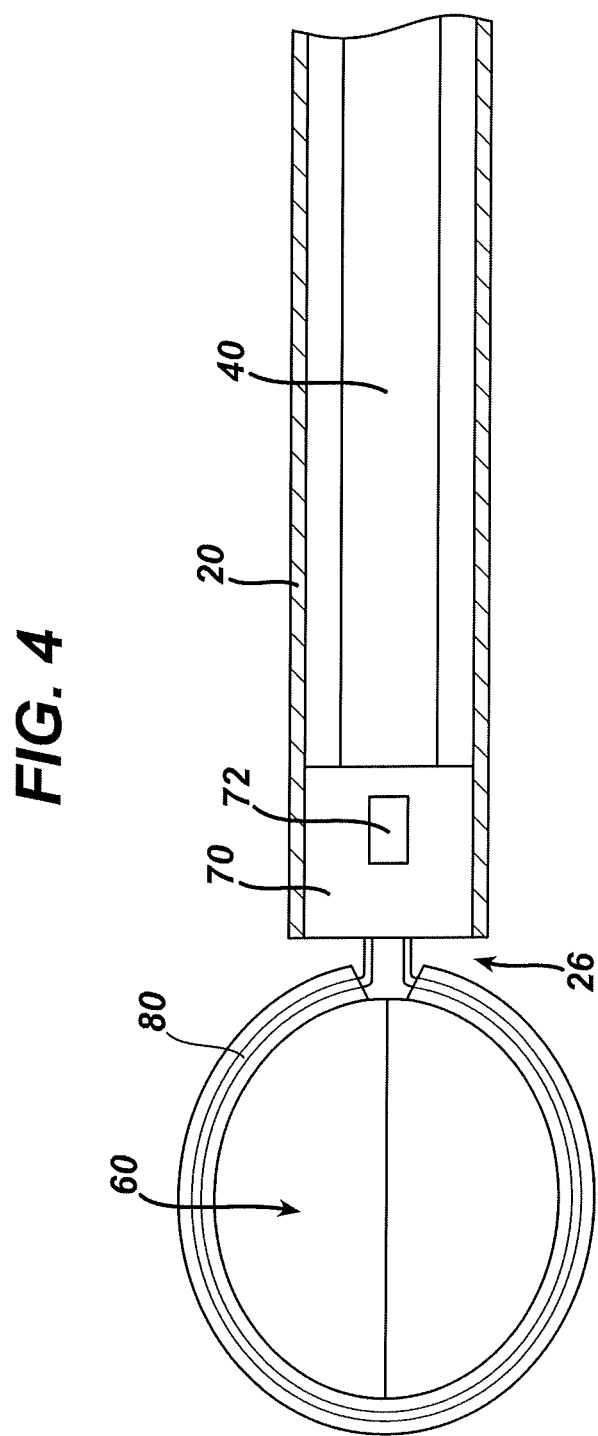
FIG. 4 is a top view of the distal end of the tissue retrieval device of FIG. 1, with the retrieval bag in the deployed position and with the introducer tube shown in cross section.

FIGS. 1-4 show an exemplary tissue retrieval device (10). In this example, tissue retrieval device (10) comprises an elongate introducer tube (20), a handle (22) secured to the proximal end of introducer tube (20), an actuating rod (40), and a thumb ring (42) secured to the proximal end of actuating rod (40). Handle (22) comprises a pair of finger grips (24). As will be described in greater detail below, actuating rod (40) is slidable within the hollow interior of introducer tube (20) to selectively deploy a tissue retrieval bag (60) from introducer tube (20). In particular, with actuating rod (40) in a proximal position as shown in FIGS. 1 and 3, a user may insert their thumb in thumb ring (42), and insert their index and middle fingers in finger grips (24), then advance thumb ring (42) distally toward finger grips (24) to translate actuating rod (40) distally to a distal position as shown in FIGS. 2 and 4.

In the present example introducer tube (20) is formed of metal; while handle (22), actuating rod (40), and thumb ring (42) are formed of plastic. However, it should be understood that any suitable material or combination of materials may be used to form these components and other components described herein. Introducer tube (20) has an open distal end (26) and a side aperture (28) just proximal to open distal end (26). Introducer tube (20) of the present example is sized such that introducer tube (20) may be introduced to a surgical site through a trocar or other type of device. By way of example only, the outer diameter of introducer tube (20) may be between approximately 5 mm (inclusive) and approximately 15 mm (inclusive). Alternatively, introducer tube (20) may have any other suitable dimension.

As shown in FIGS. 3-4, a distal plug (70) is secured to the distal end of actuating rod (40). Distal plug (70) is thus translatable from a proximal position as shown in FIG. 3 to a distal position as shown in FIG. 4 by translating actuating rod (40) distally as described above. Distal plug (70) includes a resilient tab (72) that extends upwardly from distal plug (70). Resilient tab (72) is resiliently biased to extend upwardly from distal plug (70), but is movable downwardly toward distal plug (70) in order to allow distal plug (70) to fit within and translate within introducer tube (20). However, once distal plug (70) reaches the distal position shown in FIGS. 2 and 4, resilient tab (72) is configured to "snap into" side aperture (28) of introducer tube (20), such that at least a portion of resilient tab (72) protrudes into side aperture (28). With resilient tab (72) so engaged with side aperture (28), the longitudinal position of distal plug (70) may be substantially secured. In other words, engagement between resilient tab (72) and side aperture (28) may substantially prevent proximal movement of distal plug (70) once distal plug (70) has reached a distal position. Engagement between actuating rod (40) and distal plug (70) may also prevent proximal movement of actuating rod (40) when distal plug (70) has reached the distal position. Distal plug (70) may also include a recess below resilient tab (72), which may provide clearance for resilient tab (72) to deflect downwardly when distal plug (70) is proximal to the distal position shown in FIGS. 2 and 4. Such downward deflection on resilient tab (72) may be provided by the inner diameter of introducer tube (20) when distal plug (70) is proximal to the distal position shown in FIGS. 2 and 4.

One or more indentations (29) formed at distal end (26) of introducer tube (20) may also restrict distal positioning of distal plug (70). Such restriction of distal positioning of distal plug (70) may also restrict distal positioning of actuating rod (40). In addition or in the alternative, a feature on a proximal portion of actuating rod (40) may engage handle (22) when actuating rod (40) reaches a certain distal position, to arrest further distal translation of actuating rod (40) at a selected longitudinal position. In some such versions, distal plug (70) may even be omitted. For instance, resilient hoop member (80) may be integrally secured to actuating rod (40), such that a feature located near the proximal end of tissue retrieval device (10) that arrests distal translation of actuating rod (40) (e.g., by arresting distal motion of thumb ring (42), etc.) may effectively also arrest distal positioning of resilient hoop member (80). In addition or in the alternative, distal plug (70) and side aperture (28)

may be located substantially proximal to the locations of these features shown in FIGS. 1-4.

As shown in FIGS. 2-4, a resilient hoop member (80) extends distally from distal plug (70). Resilient hoop member (80) is resiliently biased to assume an outwardly expanded circular or elliptical configuration as shown in FIGS. 2 and 4. Alternatively, resilient hoop member (80) may be resiliently biased to assume any other suitable configuration. Resilient hoop member (80) has flexibility permitting resilient hoop member (80) to compress and deformably fit within introducer tube (20) as shown in FIGS. 1 and 3. A secure attachment between resilient hoop member (80) and distal plug (70) provides unitary translation of resilient hoop member (80) and distal plug (70) relative to introducer tube (20). In addition, a secure attachment between actuating rod (40) and distal plug (70) provides unitary translation of actuating rod (40) and distal plug (70). Thus, resilient hoop member (80) may be advanced from a proximal position as shown in FIG. 3 to a distal position as shown in FIG. 4 by advancing thumb ring (42) distally toward handle (22) as described above. Such distal advancement of resilient hoop member (80) moves resilient hoop member (80) from a proximal position where it is located within introducer tube (20) to a distal position where it protrudes from open distal end (26) of introducer tube (20).

Resilient hoop member (80) may be formed of any suitable material or combination of materials, including but not limited to metal (e.g., stainless steel, nitinol, steel spring alloys, copper spring alloys, etc.), plastic, and/or metal reinforced plastic. In addition, while resilient hoop member (80) is formed as a single unitary piece, resilient hoop member (80) may alternatively be formed of any other suitable number of pieces. By way of example only, resilient hoop member (80) may be formed of two separate arms that together provide a configuration that is substantially similar to the configuration shown for resilient hoop member (80), except that the two separate arms are separated at a region corresponding to the distal-most part of resilient hoop member (80). Other suitable variations of resilient hoop member (80) will be apparent to those of ordinary skill in the art in view of the teachings herein. By way of example only, resilient hoop member (80) may be readily substituted with any bag frame component or support structure disclosed in any of the patents or patent applications cited herein. Similarly, tissue retrieval device (10) may readily incorporate any of the various bag deployment mechanisms disclosed in any of the patents or patent applications cited herein. Various suitable ways in which such alternative bag frames, support structures, deployment mechanisms, and/or other teachings in any of the patents or patent applications cited herein may be incorporated into tissue retrieval device (10) will be apparent to those of ordinary skill in the art.

Retrieval bag (60) has an open top portion (62) and a closed bottom portion (64). Open top portion (62) is sized to receive a tissue specimen. Top portion (62) is secured to resilient hoop member (80) in the present example. For instance, resilient hoop member (80) may be fed through sleeves, slots, pockets, loops, slits, etc., or one or more other features near the top opening of retrieval bag (60). The engagement between retrieval bag (60) and resilient hoop member (80) is such that retrieval bag (60) translates substantially unitarily with resilient hoop member (80) relative to introducer tube (20). Thus, retrieval bag (60) may be advanced from a proximal position as shown in FIGS. 1 and 3 to a distal position as shown in FIGS. 2 and 4 by advancing thumb ring (42) distally toward handle (22) as described above. In addition, the engagement between retrieval bag (60) and resilient hoop member (80) is such that resilient hoop member (80) substantially opens the top of retrieval bag (60) when resilient hoop member (80) reaches the expanded configuration shown in FIGS. 2 and 4. While resilient hoop member (80) is flexible enough to compressibly fit within introducer tube (20), resilient hoop member (80) has sufficient rigidity to substantially support retrieval bag (60) when resilient hoop member (80) and retrieval bag (60) protrude from open distal end (26) of introducer tube (20).

Retrieval bag (60) may have any suitable configuration when retrieval bag (60) is positioned within introducer tube (20). For instance, retrieval bag (60) may be rolled up, folded up, wadded up, or have any other suitable configuration within introducer tube (20). Various suitable configurations for retrieval bag (60) within introducer tube (20) will be described in greater detail below, while other suitable configurations for retrieval bag (60) within introducer tube (20) will be apparent to those of ordinary skill in the art in view of the teachings herein. When retrieval bag (60) has been advanced from a proximal position as shown in FIGS. 1 and 3 to a distal position as shown in FIGS. 2 and 4, a separate instrument (e.g., conventional tissue graspers, etc.) may be used to assist in unfurling retrieval bag (60). In addition or in the alternative, the material properties of retrieval bag (60), some other feature(s) of retrieval bag (60), and/or gravity may cause retrieval bag (60) to at least substantially unfurl on its own once it has been deployed from introducer tube (20). With retrieval bag (60) deployed and opened as shown in FIGS. 2 and 4, a surgeon may place tissue samples or specimens, etc. (e.g., patient's gall bladder, etc.) within retrieval bag (60) for subsequent removal of such tissue samples or specimens, etc. from the patient.

In some versions, tissue retrieval device (10) may be configured such that retrieval bag (60) is removable from resilient hoop member (80) (e.g., while these components are still within the patient, etc.). Some such versions facilitate removal of retrieval bag (60) separate from removal of the other components of the tissue retrieval device (10) from the patient. For instance, in some versions tissue retrieval device (10) may include a closure string (not shown) connected to retrieval bag (60) and having a slipknot attachment to actuating rod (40). Pulling the slipknot loose from actuating rod (40) and then retracting actuating rod (40) proximally may permit detachment of retrieval bag (60) and the closure string from the other components of specimen retrieval device (10). For instance, actuating rod (40) may be fully withdrawn from introducer tube (20) and a free end of the closure string may protrude from the proximal end of introducer tube (20). In some such versions, a user may pull the closure string to close retrieval bag (60). For instance, the closure string may be engaged with retrieval bag (60) similar to a purse string. By way of example only, such a closure mechanism may be configured in accordance with the teachings of U.S. Pat. No. 6,409,733, entitled "Specimen Retrieval Bag," issued Jun. 25, 2002, the disclosure of which is incorporated by reference herein. In some such versions, retrieval bag (60) is perforated in a region between a closure string and the region where retrieval bag (60) is coupled with resilient hoop member (80). Such perforation may permit retrieval bag (60) to be separated from hoop member (80) without compromising engagement between the closure string and retrieval bag (60). In addition or in the alternative, hoop member (80) may have a break in it or be breakable to allow retrieval bag (60) to be pulled off of hoop member (80). Other suitable ways in which retrieval bag (60) may be removable from hoop member (80) and/or closed will be apparent to those of ordinary skill in the art in view of the teachings herein.

A closed retrieval bag (60) containing tissue may be removed through the same trocar through which introducer tube (20) was inserted. In particular, a closed retrieval bag (60) containing tissue may be removed through the trocar at the same time introducer tube (20) is removed from the trocar. Alternatively, introducer tube (20) may be removed from the trocar first, then the closed retrieval bag (60) containing tissue may be removed through the trocar. As yet another merely illustrative alternative, the closed retrieval bag (60) containing tissue may be removed from the patient after introducer tube (20) and the trocar have been removed from the patient. In other words, the closed retrieval bag (60) containing tissue may be removed directly through the incision through which the trocar had been previously inserted. In any of these scenarios, a protruding closure string may be used to remove retrieval bag (60) from the patient. Alternatively, retrieval bag (60) may be removed from the patient in any other suitable fashion.

In some versions, actuating rod (40) may comprise features operable with other features of introducer tube (20) or other components to prevent inadvertent retraction of actuating rod (40) during deployment of retrieval bag (60). For example, actuating rod (40) may include a one way ratcheting mechanism as described in U.S. Pat. No. 6,409,733, entitled "Specimen Retrieval Bag," issued Jun. 25, 2002, the disclosure of which is incorporated by reference herein. Other ways in which inadvertent retraction of actuating rod (40) may be avoided through various features of tissue retrieval device (10) will be apparent to those of ordinary skill in the art in view of the teachings herein. Similarly, other various suitable components, features, configurations, and functionalities of tissue retrieval device (10) will be apparent to those of ordinary skill in the art in view of the teachings herein.

B. Exemplary Tissue Retrieval Device with Retractable Sheath

Figure 5:
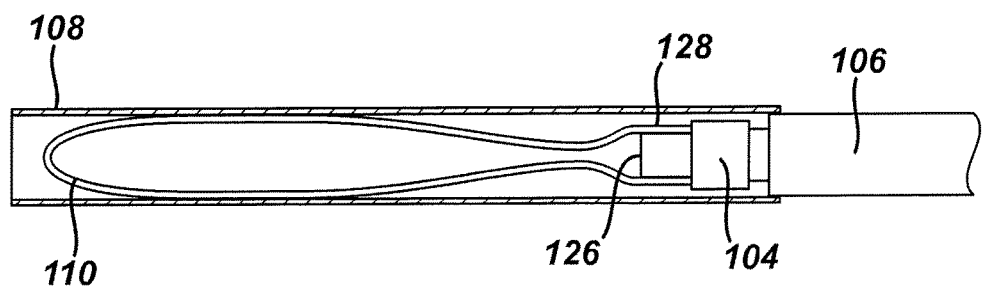
FIG. 5 is a top view of the distal end of an exemplary alternative tissue retrieval device, with a sheath in a distal position and shown in cross section, and with a retrieval bag omitted.
Figure 6:
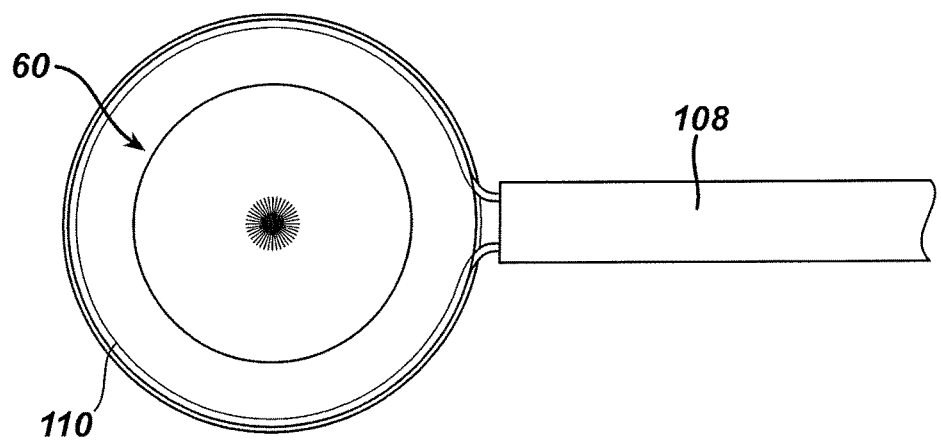
FIG. 6 is a top view of the distal end of the tissue retrieval device of FIG. 5, with the sheath in a proximal position.

FIGS. 5-6 show exemplary alternative features that may be incorporated into a tissue retrieval device such as tissue retrieval device (10). In particular, this alternative tissue retrieval device includes a rod (104), an introducer tube (106), a sheath (108), a resilient hoop (110), and a retrieval bag (60). Rod (104) is fixedly positioned within introducer tube (106) in the present example. However, in some other versions, rod (104) may be configured to reciprocate within introducer tube (106) (e.g., like rod (40) of tissue retrieval device (10) described above, etc.). Sheath (108) is configured to translate relative to introducer tube (106). In particular, and as will also be described in greater detail below, sheath (108) is translatable from a distal position (FIG. 5) to a proximal position (FIG. 6). Together, introducer tube (106) and sheath (108) are configured to fit within the insertion passageway defined by a device such as a trocar. By way of example only, introducer tube (106) and sheath (108) may present an outer diameter that is between approximately 5 mm (inclusive) and approximately 15 mm (inclusive). Alternatively, these components may have any other suitable dimensions. Resilient hoop (110) carries retrieval bag (60), and is resiliently biased to expand from a compressed configuration (FIG. 5) to an expanded configuration (FIG. 6), as will also be described in greater detail below.

FIG. 5 shows the alternative specimen retrieval instrument of the present example in an undeployed configuration. In this configuration, sheath (108) is in a distal position, substantially enclosing resilient resilient hoop (110) and retrieval bag (60). In this configuration, the specimen retrieval instrument is ready to be inserted within a patient. By way of example only, the specimen retrieval instrument may be inserted into a patient via a trocar or other type of access port device, via an incision, via a natural orifice, and/or in any other suitable fashion. Introducer tube (106) has a substantially cylindraceous configuration in the present example. However, it should be understood that introducer tube (106) may have any suitable configuration. In addition, it should be understood that any suitable type of handle assembly may be provided at the proximal end of introducer tube (106) and/or sheath (108). By way of example only, such a handle assembly may have one or more finger grips, thumb rings, or any other suitable structures, features, or configurations. Such a handle assembly may be configured to facilitate proximal translation of sheath (108) relative to introducer tube (106). In addition or in the alternative, one or more cables, strings, rods, or other features may be operable to provide proximal translation of sheath (108) relative to introducer tube (106).

FIG. 6 shows the alternative specimen retrieval instrument of the present example in a deployed configuration. In this configuration, sheath (108) is in a proximal position, substantially revealing resilient resilient hoop (110) and retrieval bag (60). In the present example, the specimen retrieval instrument is transitioned from the undeployed configuration to the deployed configuration after the distal end of the specimen retrieval instrument has been inserted within a patient. To transition the specimen retrieval instrument from the undeployed configuration to the deployed configuration, sheath (108) is retracted proximally relative to introducer tube (106). It should be understood that such proximal retraction of sheath (108) may be accomplished in a variety of ways. By way of example only, sheath (108) may have a length selected such that a proximal portion of sheath (108) protrudes proximally relative to a trocar or other access port when the distal end of the specimen retrieval instrument is inserted in a patient. Thus, such a proximal portion of sheath (108) may be manipulated by a surgeon or other user externally relative to the patient during a surgical procedure. A handle, grip, or other structural feature may be provided at the proximal end of sheath (108) to facilitate such extracorporeal manipulability of sheath (108). In addition or in the alternative, a string, cable, or other feature may be coupled with sheath (108) and may be operable to retract sheath (108) proximally. In addition or in the alternative, a feature that is operable to retract sheath (108) proximally may extend within the interior of introducer tube (106), in addition to or as an alternative to extending along the exterior of introducer tube (106).

In some alternative versions, sheath (108) is removable from introducer tube (106) by pulling sheath (108) off of introducer tube (106) in a distal direction; rather than providing proximal retractability of sheath (108). By way of example only, sheath (108) may be configured like a sleeve or sock, and a separate instrument (e.g., conventional tissue graspers, etc.) may be used to pull sheath (108) distally off of resilient resilient hoop (110) and retrieval bag (60). In addition or in the alternative, sheath (108) may have a perforation or other weakening feature that may be breached to remove sheath (108) by tearing sheath (108) away from introducer tube (106). As yet another merely illustrative alternative, sheath (108) may be formed of an environmentally sensitive material. For instance, sheath (108) may be configured to dissolve or substantially weaken in the presence of bodily fluid, certain temperatures, or other environmental parameters that may be associated with the interior of a patient. Still other various ways in which sheath (108) may be configured and/or operable will be apparent to those of ordinary skill in the art in view of the teachings herein. Furthermore, sheath (108) may even be omitted in some versions.

Retrieval bag (60) is substantially identical to retrieval bag (60) described above in the context of specimen retrieval instrument (10). In addition, engagement between retrieval bag (60) and resilient hoop (110) is substantially identical to the engagement between retrieval bag (60) and resilient hoop (80) described above in the context of specimen retrieval instrument (10). Alternatively, these components may have any other suitable configurations and relationships.

As noted above, resilient hoop (110) is resiliently biased to maintain a substantially circular shape when not constricted by other components. Of course, resilient hoop (110) may be resiliently biased to maintain any other suitable shape. As shown in FIG. 5, resilient hoop (110) is connected to distal end (126) of rod (104). In the present example, the connection of resilient hoop (110) to rod (104) is achieved by resilient hoop (110) having parallel proximal ends (128) that secure to respective sides of distal end 126 of rod (104) by the use of securing pins (not shown) or other suitable attachment means. As noted above, rod (104) is fixedly positioned within introducer tube (106) in the present example. Accordingly, resilient hoop (110) and retrieval bag (60) are fixedly positioned relative to introducer tube (106) in the present example. However, it should be understood that these components may be substituted with various other components or structures; and that these components may have a variety of alternative relationships with each other. By way of example only, in some versions rod (104) is configured to translate relative to introducer tube (106), much like translation of rod (40) relative to introducer tube (20) described above in the context of specimen retrieval instrument (10), with resilient hoop (110) and retrieval bag (60) being locatable within the hollow interior defined by introducer tube (106).

In use, the alternative specimen retrieval instrument of the present example may initially have the arrangement shown in FIG. 5, where sheath (108) is at a distal position. In this arrangement, the distal portion of the specimen retrieval instrument 100 may be inserted within a patient through a suitable incision opening or access port created by a trocar or some other device. Once positioned within the patient, sheath (108) may be retracted proximally. This action reveals resilient hoop (110) and retrieval bag (60). With resilient hoop (110) being so freed from the confines of sheath (108), the resilient bias of resilient hoop (110) causes loop to expand to the configuration shown in FIG. 6, thereby opening retrieval bag (60). Once retrieval bag (60) has been opened, one or more tissue specimens, etc., may be placed within retrieval bag (60). Once a specimen has been placed within retrieval bag (60), sheath (108) may be advanced distally relative to introducer tube (106), with introducer tube (106) maintaining a substantially constant position relative to the patient (or introducer tube (106) may be retracted proximally relative to sheath (108), with sheath (108) maintaining a substantially constant position relative to the patient). Such a motion may thus cause sheath (108) to at least substantially envelop resilient hoop (110) once again. In particular, such engagement between sheath (108) and resilient hoop (110) may cause resilient hoop (110) to transition back toward a substantially collapsed configuration. Overcoming the resilient bias of resilient hoop (110) in this way may permits resilient hoop (110) and retrieval bag (60) to close, and in some versions for a proximal portion of resilient hoop (110) to be constrained within a distal portion of sheath (108). With retrieval bag (60) closed, the specimen retrieval instrument is now ready to be removed from the patient. Of course, there does not necessarily have to be any relative movement between sheath (108) and introducer tube (106) after a specimen has been placed in retrieval bag (60) and before the specimen retrieval instrument is removed from the patient.

In some versions, the alternative specimen retrieval instrument of the present example is configured such that retrieval bag (60) may be removed from the specimen retrieval instrument while retrieval bag (60) is within the patient. Some such versions facilitate removal of retrieval bag (60) separate from removal of the other components of the specimen retrieval instrument. In some versions, this may be accomplished by, among other ways, retrieval bag (60) being removable from resilient hoop (110). For instance, in some versions the specimen retrieval instrument may include a closure string as described above and as taught in U.S. Pat. No. 6,409,733, entitled "Specimen Retrieval Bag," issued Jun. 25, 2002, which is incorporated herein by reference. Other suitable ways in which retrieval bag (60) may be removable from hoop (110) and/or closed will be apparent to those of ordinary skill in the art in view of the teachings herein. In addition, various suitable ways in which a retrieval bag (60) may be removed from a patient will be apparent to those of ordinary skill in the art in view of the teachings herein.

In some versions, modifications may include rod (104) or introducer tube (106) having features operable with features of sheath (108) or other components to prevent inadvertent retraction of sheath (108) and premature opening of resilient hoop (110) and retrieval bag (60). For example, rod (104) may include a lock or stop that may be released once a user is ready to open resilient hoop (110) and retrieval bag (60). Still in other versions, modifications may include rod (104) having features operable with features of sheath (108) or other components to prevent inadvertent advancement of sheath (108) after initial deployment of resilient hoop (110) and opening of retrieval bag (60). For example, rod (104) may be associated with a resilient tab configured to engage a corresponding opening in a sidewall of sheath (108) upon deployment of resilient hoop (110). The engagement between the resilient tab and the opening in the sidewall of sheath (108) may act as a locking mechanism that prevents inadvertent advancement of sheath (108), and therefore inadvertent premature closure of resilient hoop (110) and retrieval bag (60). Other ways in which inadvertent retraction and/or advancement of sheath (108) may be avoided through various features of a specimen retrieval instrument will be apparent to those of ordinary skill in the art in view of the teachings herein.

C. Other Exemplary Tissue Retrieval Devices

It should be understood that the components, features, and configurations of tissue retrieval devices shown in FIGS. 1-6 are merely exemplary. As one merely illustrative alternative, a tissue retrieval device, tissue retrieval bag, and/or related components/features may be configured in accordance with the teachings of U.S. patent application Ser. No. 12/692,670 (now U.S. Pat. No. 8,444,655), entitled "Tissue Retrieval Device with Modular Pouch Cartridge," filed Jan. 25, 2010, the disclosure of which is incorporated by reference herein. As another merely illustrative example, a tissue retrieval device, tissue retrieval bag, and/or related components/features may be configured in accordance with the teachings of U.S. patent application Ser. No. 12/693,476 (now U.S.

Pat. No. 8,425,533), entitled "Tissue Retrieval Device with Pouch Stretching Arm," filed Jan. 26, 2010, the disclosure of which is incorporated by reference herein. As yet another merely illustrative example, a tissue retrieval device, tissue retrieval bag, and/or related components/features may be configured in accordance with the teachings of U.S. patent application Ser. No. 12/692,709 (now U.S. Pat. No. 8,409,216), entitled "Tissue Retrieval Device with Buckling Arms," filed Jan. 25, 2010, the disclosure of which is incorporated by reference herein. As yet another merely illustrative example, a tissue retrieval device, tissue retrieval bag, and/or related components/features may be configured in accordance with the teachings of U.S. patent application Ser. No. 12/692,733 (now U.S. Pat. No. 8,409,217), entitled "Tissue Retrieval Device with Bladders," filed Jan. 25, 2010, the disclosure of which is incorporated by reference herein. As yet another merely illustrative example, a tissue retrieval device, tissue retrieval bag, and/or related components/features may be configured in accordance with the teachings of U.S. patent application Ser. No. 12/692,727 (published as U.S. Pub. No. 2011/0184311), entitled "Tissue Retrieval Device with Resilient Member," filed Jan. 25, 2010, the disclosure of which is incorporated by reference herein. As yet another merely illustrative example, a tissue retrieval device, tissue retrieval bag, and/or related components/features may be configured in accordance with the teachings of U.S. patent application Ser. No. 12/693,485 (now U.S. Pat. No. 8,414,596, entitled "Tissue Retrieval Device with Gusseted Pouch," filed Jan. 26, 2010, the disclosure of which is incorporated by reference herein. As yet another merely illustrative example, a tissue retrieval device, tissue retrieval bag, and/or related components/features may be configured in accordance with the teachings of U.S. patent application Ser. No. 12/693,498 (now U.S. Pat. No. 8,419,749), entitled "Tissue Retrieval Device with Reinforced Pouch and Variable Volume," filed Jan. 26, 2010, the disclosure of which is incorporated by reference herein. Furthermore, various ways in which the teachings herein may be combined with the teachings of any of the above-referenced patent applications will be apparent to those of ordinary skill in the art.

Still other suitable components, features, configurations, and operabilities that may be provided by a tissue retrieval device and/or tissue retrieval bag, etc. will be apparent to those of ordinary skill in the art in view of the teachings herein.

II. Exemplary Methods of Loading Retrieval Bags

In some settings, it may be desirable to minimize the outer diameter of an instrument that is inserted in a patient. As noted above, this may include providing an introducer tube (20) or sheath (108) having an outer diameter less than approximately 15 mm (inclusive), less than approximately 10 mm (inclusive), or even at or less than approximately 5 mm (inclusive). Using outer diameters of these sizes may of course further restrict the inner diameter provided by a specimen retrieval instrument, which may in turn provide unique challenges of fitting a retrieval bag (60) and a frame for retrieval bag (60) (such as a hoop member (80) or hoop (110), etc.) together within the restricted inner diameter. The various examples described below relate to various ways in which a retrieval bag (60) may be loaded or packed in a tissue retrieval device. In some instances, these methods of loading or packing a retrieval bag (60) may address design challenges associated with fitting a retrieval bag (60) and a frame for retrieval bag (60) (such as a hoop member (80) or hoop (110), etc.) together within a significantly restricted inner diameter as noted above. In other words, these methods of loading or packing a retrieval bag (60) may provide a special benefit, or even unexpected result, of allowing a retrieval bag (60) and a frame for retrieval bag (60) (such as a hoop member (80) or hoop (110), etc.) to be fit together within the inner diameter of a tubular member (e.g., introducer tube (20) or sheath (108), etc.) or other component that is subject to design restrictions requiring an outer diameter that is less than approximately 15 mm (inclusive), less than approximately 10 mm (inclusive), or even at or less than approximately 5 mm (inclusive). The below described methods may thus address these challenges better than conventional methods of packing and loading a retrieval bag (60). Of course, the below methods may also be applied in settings where such challenges are not present.

The below examples will be discussed mainly in the context of a tissue retrieval device (10) as shown in FIGS. 1-2 and described above. However, it should be understood that the below teachings of methods and configurations for loading/packing a retrieval bag (60) may be readily incorporated into virtually any other type of tissue retrieval device. By way of example only, the below teachings of methods and configurations for loading/packing a retrieval bag (60) may be readily incorporated into the context of a tissue retrieval device with a retractable sheath (108) as shown in FIGS. 3-4 and described above. Furthermore, the below teachings of methods and configurations for loading/packing a retrieval bag (60) may be readily incorporated into any of the tissue retrieval devices that are taught in the various patents and patent applications that are cited herein. Various suitable ways in which the below teachings of methods and configurations for loading/packing a retrieval bag (60) may be incorporated into such alternative tissue retrieval devices will be apparent to those of ordinary skill in the art in view of the teachings herein. Furthermore, other examples of tissue retrieval devices that may incorporate the below teachings of methods and configurations for loading/packing a retrieval bag (60) will be apparent to those of ordinary skill in the art in view of the teachings herein.

It should also be understood that the below teachings of methods and configurations for loading/packing a retrieval bag (60) in a tissue retrieval device may be readily applied to virtually any type of tissue retrieval bag. By way of example only, it should be understood that the below teachings of methods and configurations for loading/packing a retrieval bag (60) may be readily applied to any of the various tissue retrieval bags taught in any of the various patents and patent applications that are cited herein. Various suitable ways in which the below teachings of methods and configurations for loading/packing a retrieval bag (60) may be applied to such alternative tissue retrieval bags will be apparent to those of ordinary skill in the art in view of the teachings herein. Furthermore, other examples of tissue retrieval bags to which the below teachings of methods and configurations for loading/packing a retrieval bag (60) may be applied will be apparent to those of ordinary skill in the art in view of the teachings herein.

In addition, it should be understood that the below teachings of methods and configurations for loading/packing a retrieval bag (60) in a tissue retrieval device may be performed/provided before a tissue retrieval instrument is shipped to an end user. For instance, such methods/configurations may be performed/provided as part of a manufacturing process before the tissue retrieval instrument leaves a manufacturing facility. Alternatively, such methods/configurations may be performed/provided by an end user or elsewhere along the supply chain. Alternatively, such methods/configurations may be performed/provided by any other suitable person or entity and at any other suitable time.

A. Exemplary Folding of Retrieval Bags

Figure 7:
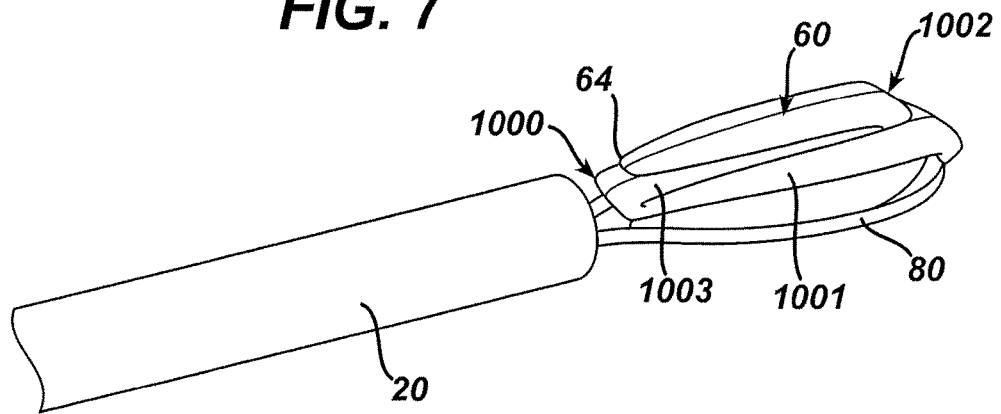
FIG. 7 is a perspective view of the distal end of an exemplary tissue retrieval device, with a retrieval bag in an exemplary folded configuration.
Figure 8:
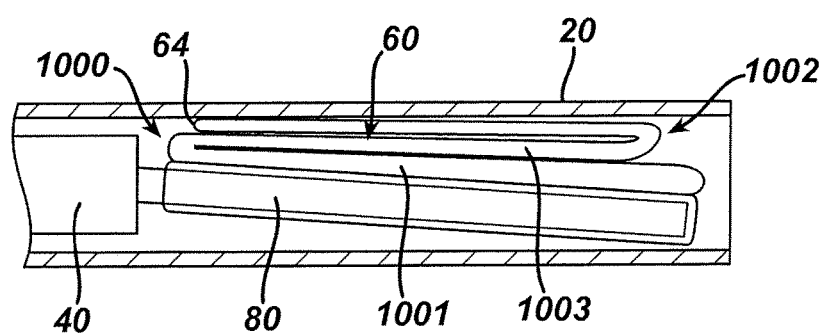
FIG. 8 is a side view of the distal end of the tissue retrieval device of FIG. 7, with the retrieval bag in the folded configuration of FIG. 7, and with a sheath positioned distally over the retrieval bag and shown in cross section.

As part of a process of packing or otherwise loading a retrieval bag (60) within an introducer tube (60) or sheath (108), the retrieval bag (60) may be folded in a variety of ways. FIGS. 7-8 depict one merely exemplary way in which a retrieval bag (60) may be folded for purposes of packing retrieval bag (60) within introducer tube (20). In particular, retrieval bag (60) is folded in a zigzag fashion. This zigzag configuration is created by a plurality of bends or folds (1000, 1002) that are oriented transverse to the longitudinal axis defined by introducer tube (20). While folds (1000, 1002) are oriented transverse to the longitudinal axis defined by introducer tube (20), folded portions (1001, 1003) that are adjacent to folds (1000, 1002) are oriented parallel to the longitudinal axis defined by introducer tube (20). To produce such folds (1000, 1002), closed bottom portion (64) may first be brought over the distal portion of resilient hoop member (80) to a proximal position. Retrieval bag (60) may then be bent, and closed bottom portion (64) may then be moved distally with a portion (1001) of retrieval bag (60) remaining in place to create a first fold (1000). In particular, first fold (1000) is created by bending retrieval bag (60) over an axis that is substantially transverse to the longitudinal axis defined by introducer tube (20). Retrieval bag (60) may then be bent again, and closed bottom portion (64) may then be moved proximally with another portion (1003) of retrieval bag (60) remaining in place to create a second fold (1002). Second fold (1002) is thus also created by bending retrieval bag (60) over an axis that is substantially transverse to the longitudinal axis defined by introducer tube (20). Closed bottom portion (64) may then be placed adjacent to portion (1003) as shown in FIGS. 7-8.

As is also shown in FIGS. 7-8, folded retrieval bag (60) is positioned on top of hoop member (80) in the present example. Even with such positioning of retrieval bag (60), retrieval bag (60) and hoop member (80) still fit within the inner diameter defined by introducer tube (20) as shown in FIG. 8. While FIG. 8 shows hoop member (80) flexing downwardly to provide clearance for folded retrieval bag (60), it should be understood that hoop member (80) may alternatively maintain a substantially longitudinally straight configuration when retrieval bag (60) and hoop member (80) are positioned together within introducer tube (20).

In some variations of the folding shown in FIGS. 7-8, the folding process is begun by pulling closed bottom portion (64) of retrieval bag (60) up through bottom portion of retrieval bag (60); rather than by first bringing closed bottom portion (64) over the distal portion of resilient hoop member (80). As another merely illustrative variation, folds (1000, 1002) and portions (1001, 1003) may be positioned below hoop member (80) rather than being positioned above hoop member (80) as shown. It should also be understood that any suitable number of folds may be provided in retrieval bag (60), and that the two folds (1000, 1002) shown and described are merely illustrative examples.

In use, retrieval bag (60) may be positioned with hoop member (80) within introducer tube (20), as shown in FIG. 8, until the distal portion of specimen retrieval instrument (10) is inserted into a patient as described above. Then, actuating rod (40) may be advanced distally relative to introducer tube (20) to expose retrieval bag (60) and hoop member (80) as shown in FIG. 7. Hoop member (80) may then resiliently expand to a substantially circular configuration, substantially elliptical configuration, or some other configuration (e.g., the configuration shown in FIGS. 2 and 4, etc.); and retrieval bag (60) may be unfolded and opened to receive a tissue specimen. By way of example only, retrieval bag (60) may be unfolded using a separate instrument (e.g., conventional tissue graspers, etc.), due to gravity, due to material properties of retrieval bag (60), due to expansion of one or more resilient members secured to or in retrieval bag (60), and/or by any other means. With retrieval bag (60) being unfolded and opened, a tissue specimen may be placed within retrieval bag (60); and retrieval bag (60) may be closed and removed from the patient as described herein or otherwise.

Figure 9:
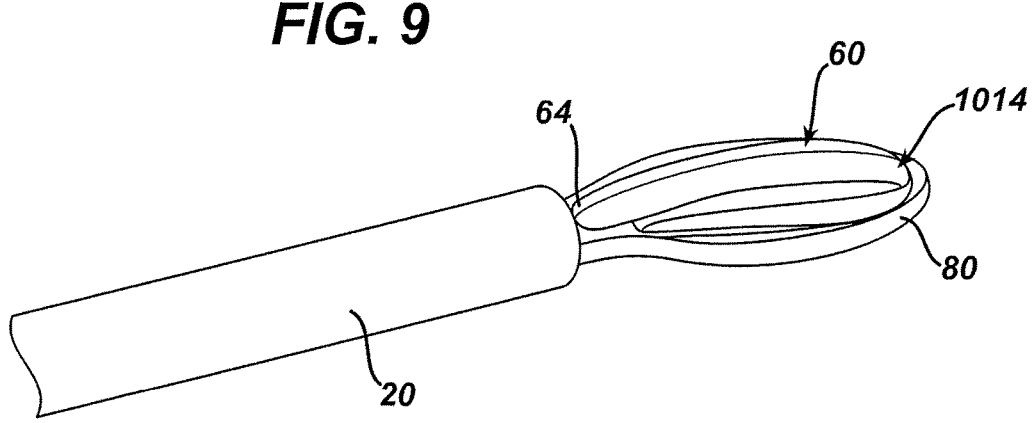
FIG. 9 is a perspective view of the distal end of an exemplary tissue retrieval device, with a retrieval bag in another exemplary folded configuration.
Figure 10:
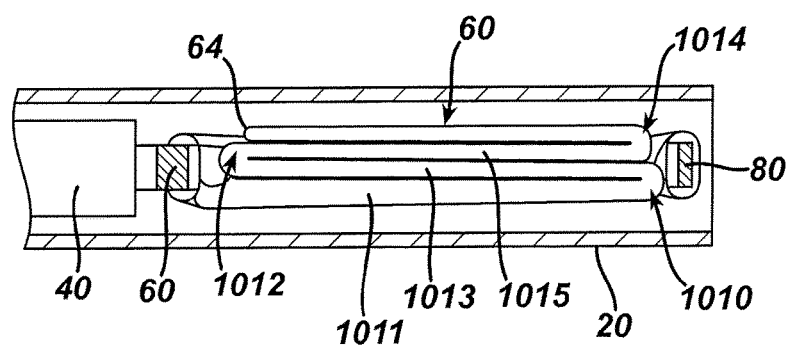
FIG. 10 is a side view of the distal end of the tissue retrieval device of FIG. 9, with the retrieval bag in the folded configuration of FIG. 9, and with a sheath positioned distally over the retrieval bag and shown in cross section.

FIGS. 9-10 depict a variation of the retrieval bag (60) folding method shown in FIGS. 7-8. In this example, retrieval bag (60) is again folded in a zigzag fashion, with the zigzag configuration being created by a plurality of folds (1010, 1012, 1014). In addition, each fold (1010, 1012, 1014) in this example is created by bending retrieval bag (60) about respective axes that are substantially transverse to the longitudinal axis defined by introducer tube (20). In other words, folds (1010, 1012, 1014) are created by alternatingly moving closed bottom portion (64) distally, then proximally, then distally, then proximally, while leaving portions (1011, 1013, 1015) of retrieval bag (60) in place during this process. Folds (1010, 1012, 1014) are also offset from each other in this example, such that folds (1010, 1012, 1014) get progressively closer to an axis that passes through the center of the opening defined by resilient hoop member (80), such axis being perpendicular to the longitudinal axis defined by introducer tube (20). While folds (1010, 1012, 1014) are oriented transverse to the longitudinal axis defined by introducer tube (20), folded portions (1011, 1013, 1015) that are adjacent to folds (1010, 1012, 1014) are oriented parallel to the longitudinal axis defined by introducer tube (20).

However, unlike the configuration shown in FIGS. 7-8, portions (1011, 1013, 1015) of retrieval bag (60) are positioned within the opening defined by hoop member (80). In other words, folded retrieval bag (60) is stuffed in hoop member (80) in this example rather than resting on top of hoop member (80). Nevertheless, folded retrieval bag (60) and hoop member (80) still fit within the inner diameter defined by introducer tube (20) as shown in FIG. 10. A tissue retrieval instrument (10) having a retrieval bag (60) with the configuration shown in FIGS. 9-10 may be used in the same way as a tissue retrieval instrument (10) having a retrieval bag (60) with the configuration shown in FIGS. 7-8. Examples of such uses are described above, while other suitable uses will be apparent to those of ordinary skill in the art in view of the teachings herein.

Figure 11:
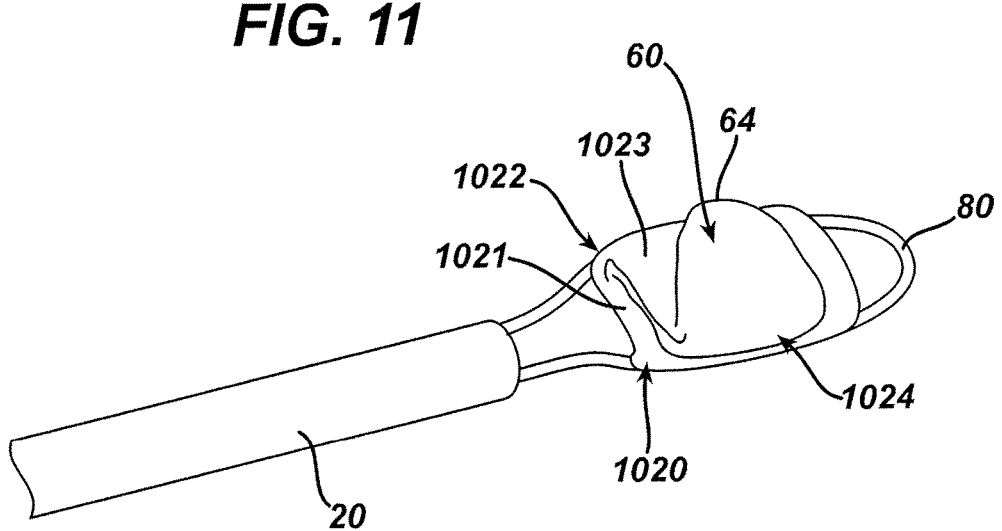
FIG. 11 is a perspective view of the distal end of an exemplary tissue retrieval device, with a retrieval bag in yet another exemplary folded configuration.

FIG. 11 depicts yet another merely illustrative variation of a retrieval bag (60) folding method. This example is similar to the folding method shown in FIGS. 7-8, except that retrieval bag (60) is folded transversely in the FIG. 11 method rather than being folded longitudinally as in the FIGS. 7-8 method. The retrieval bag (60) shown in FIG. 11 also has a zigzag configuration, which is created by folds (1020, 1022, 1024). Each fold (1020, 1022, 1024) in this example is created by bending retrieval bag (60) about respective axes that are substantially parallel to the longitudinal axis defined by introducer tube (20). In other words, folds (1020, 1022, 1024) are created by alternatingly moving closed bottom portion (64) in a first lateral direction, then in an opposite second lateral direction, then back in the first lateral direction, while leaving portions (1021, 1023) of retrieval bag (60) in place during this process. At the start of the folding process, closed bottom portion (64) may be pulled over the top of a side portion of hoop member (80) or some other portion of hoop member (80). Alternatively, closed bottom portion (64) may be pulled up through open portion (62) of retrieval bag (60).

FIG. 11 shows folds (1020, 1022, 1024) and portions (1021, 1023) being positioned on top of hoop member (80). It should be understood, however, that at least some of folds (1020, 1022, 1024) and portions (1021, 1023) may be positioned below hoop member (80). Furthermore, folds (1020, 1022, 1024) and portions (1021, 1023) may be positioned within the opening defined by hoop member (80), similar to the configuration shown in FIGS. 9-10. A tissue retrieval instrument (10) having a retrieval bag (60) with the configuration shown in FIG. 11 may be used in the same way as a tissue retrieval instrument (10) having a retrieval bag (60) with the configuration shown in FIGS. 7-8. Examples of such uses are described above, while other suitable uses will be apparent to those of ordinary skill in the art in view of the teachings herein.

Figure 12:
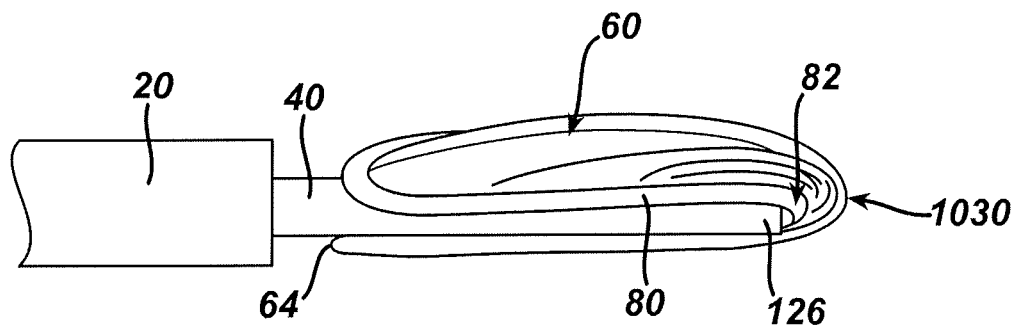
FIG. 12 is a perspective view of the distal end of an exemplary tissue retrieval device, with a deployment hoop folded rearwardly and with a retrieval bag folded about the distal end of an actuating rod.
Figure 13:
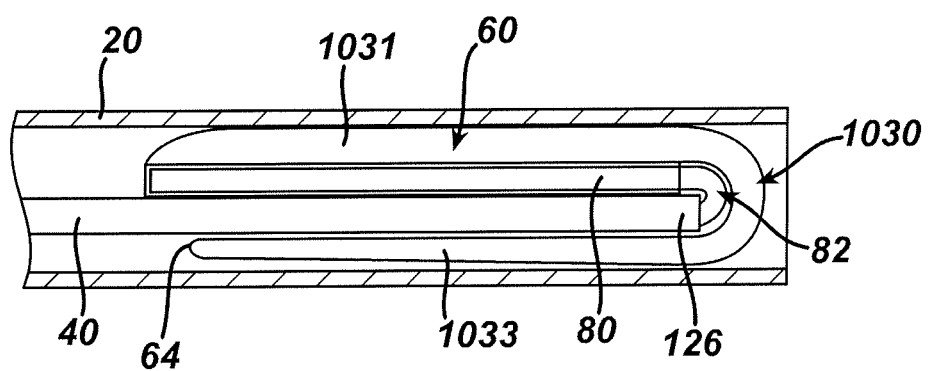
FIG. 13 is a side view of the distal end of the tissue retrieval device of FIG. 12, with the deployment hoop and retrieval bag in the configurations of FIG. 12, and with a sheath positioned distally over the retrieval bag and shown in cross section.

FIGS. 12-13 depict another merely illustrative retrieval bag (60) folding method. In this example, hoop member (80) is bent rearwardly from distal end (126) of actuating rod (104), creating a bend (82). This bend (82) redirects hoop member (80) approximately 180°, such that hoop member (80) rests against and is substantially parallel to actuating rod (40). With hoop member (80) being so bent, open top portion (62) of retrieval bag (60) may open in a downward presentation; while closed bottom portion (64) of retrieval bag (60) may be initially positioned above open top portion (62), such that retrieval bag (60) is upside-down. In the present example, closed bottom portion (64) is moved distally then downwardly then proximally to wrap around bend (82) as shown in FIGS. 12-13. This creates a distal fold (1030) in retrieval bag (60). In this configuration, a first portion (1031) of retrieval bag (60) is positioned above actuating rod (40) while a second portion (1033) of retrieval bag (60) is positioned below actuating rod (40).

As can be seen in FIG. 13, retrieval bag (60) and hoop member (80) still fit within the inner diameter defined by introducer tube (20) when bend (82) and fold (1030) are present. In use, a specimen retrieval instrument (10) may initially have this configuration shown in FIG. 13 as a distal portion of specimen retrieval instrument (10) is inserted into a patient as described above. Then, actuating rod (40) may be advanced distally relative to introducer tube (20) to expose retrieval bag (60) and hoop member (80) as shown in FIG. 12. Hoop member (80) may then resiliently flip forward, straightening out bend (82), and expand outwardly to provide hoop member (80) with a configuration similar to the one shown in FIGS. 2 and 4. This action of hoop member (80) may also unfold and open retrieval bag (60) to receive a tissue specimen. With retrieval bag (60) being unfolded and opened, a tissue specimen may be placed within retrieval bag (60); and retrieval bag (60) may be closed and removed from the patient as described herein or otherwise. A tissue retrieval instrument (10) having a retrieval bag (60) with the configuration shown in FIGS. 12-13 may be used in the same way as a tissue retrieval instrument (10) having a retrieval bag (60) with the configuration shown in FIGS. 7-8. Examples of such uses are described above, while other suitable uses will be apparent to those of ordinary skill in the art in view of the teachings herein.

Figure 14:
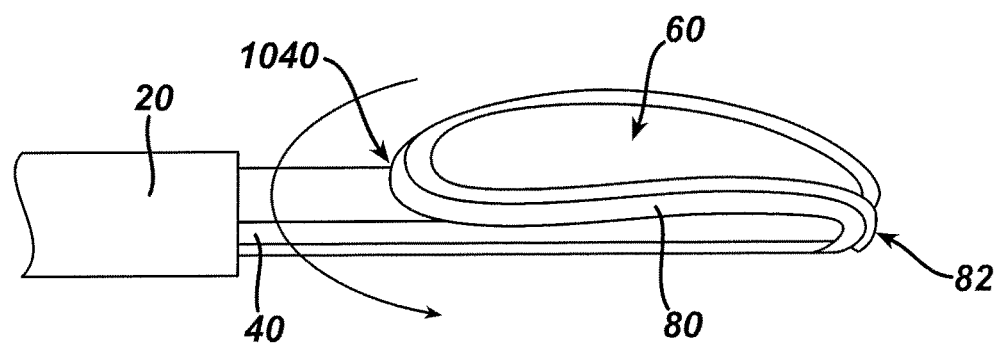
FIG. 14 is a perspective view of the distal end of an exemplary tissue retrieval device, with a deployment hoop folded rearwardly and with a retrieval bag folded under the deployment hoop.
Figure 15:
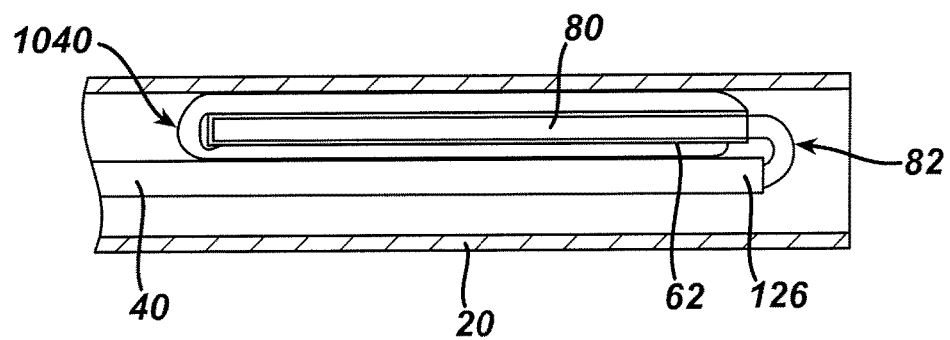
FIG. 15 is a side view of the distal end of the tissue retrieval device of FIG. 14, with the deployment hoop and retrieval bag in the configurations of FIG. 14, and with a sheath positioned distally over the retrieval bag and shown in cross section.

FIGS. 14-15 depict a variation of the retrieval bag (60) folding method shown in FIGS. 12-13. In this example, hoop member (80) is again bent rearwardly from distal end (126) of actuating rod (104), creating a bend (82). This bend (82) redirects hoop member (80) approximately 180°, such that hoop member (80) rests against and is substantially parallel to actuating rod (40). Unlike the method shown in FIGS. 12-13, however, in the method shown in FIGS. 14-15 closed bottom portion (64) of retrieval bag (60) is moved proximally then fed up into open top portion (62) of retrieval bag (60) and into the opening defined by hoop member (80). This creates a proximal fold (1040) in retrieval bag (60). In this configuration, closed bottom portion (64) of retrieval bag (60) is tucked above actuating rod (40). In particular, closed bottom portion (64) and other tucked portions of retrieval bag (60) may be folded, rolled, twisted, wadded, or otherwise positioned within open top portion (62) of retrieval bag (60) and the opening defined by hoop member (80).

As can be seen in FIG. 15, retrieval bag (60) and hoop member (80) still fit within the inner diameter defined by introducer tube (20) when bend (82) and fold (1040) are present. In use, a specimen retrieval instrument (10) may initially have this configuration shown in FIG. 15 as a distal portion of specimen retrieval instrument (10) is inserted into a patient as described above. Then, actuating rod (40) may be advanced distally relative to introducer tube (20) to expose retrieval bag (60) and hoop member (80) as shown in FIG. 14. Hoop member (80) may then resiliently flip forward, straightening out bend (82), and expand outwardly to provide hoop member (80) with a configuration similar to the one shown in FIGS. 2 and 4. This action of hoop member (80) may also unfold and open retrieval bag (60) to receive a tissue specimen. With retrieval bag (60) being unfolded and opened, a tissue specimen may be placed within retrieval bag (60); and retrieval bag (60) may be closed and removed from the patient as described herein or otherwise. A tissue retrieval instrument (10) having a retrieval bag (60) with the configuration shown in FIGS. 14-15 may be used in the same way as a tissue retrieval instrument (10) having a retrieval bag (60) with the configuration shown in FIGS. 7-8. Examples of such uses are described above, while other suitable uses will be apparent to those of ordinary skill in the art in view of the teachings herein.

While FIGS. 7-15 depict several merely illustrative ways in which a retrieval bag (60) may be folded. It is contemplated that a retrieval bag (60) may be folded in a variety of alternative ways. Various other suitable ways in which a retrieval bag (60) may be folded will be apparent to those of ordinary skill in the art in view of the teachings herein. Furthermore, a retrieval bag (60) may be subject to various other processes (e.g., rolling, wrapping, etc.) in addition to or in lieu of being folded. Some examples of such other processes are described herein, while other examples of such other processes will be apparent to those of ordinary skill in the art in view of the teachings herein.

B. Exemplary Rolling of Retrieval Bags

Figure 16:
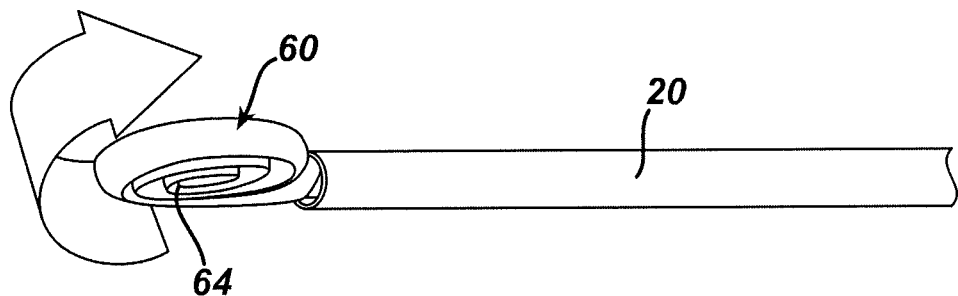
FIG. 16 is a perspective view of the distal end of an exemplary tissue retrieval device, with a retrieval bag in an exemplary rolled configuration.
Figure 17:
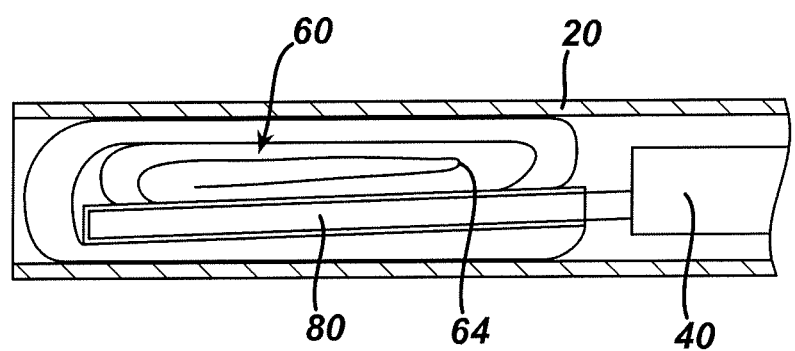
FIG. 17 is a side view of the distal end of the tissue retrieval device of FIG. 16, with the retrieval bag in the rolled configuration of FIG. 16, and with a sheath positioned distally over the retrieval bag and shown in cross section.

In addition to or in lieu of folding a retrieval bag (60) as part of a process of packing or otherwise loading the retrieval bag (60) within an introducer tube (60) or sheath (108), the retrieval bag (60) may be rolled in a variety of ways. For instance, FIGS. 16-17 show an exemplary method whereby retrieval bag (60) is rolled about an axis that is substantially transverse to the longitudinal axis defined by introducer tube (20). This rolling process may be initiated by first moving closed bottom portion (64) distally then starting with bottom portion (64) to roll retrieval bag (60) in a proximal motion. This rolling may continue until rolled retrieval bag (60) is positioned over hoop member (80) as shown in FIG. 17. With retrieval bag (60) rolled over hoop member (80), retrieval bag (60) and hoop member (80) may be compressed within introducer tube (20). While rolled retrieval bag (60) is positioned at the top of hoop member (80) in the present example, it should be understood that rolled retrieval bag (60) may alternatively be positioned at the bottom of hoop member (80).

In use, retrieval bag (60) may be positioned with hoop member (80) within introducer tube (20), as shown in FIG. 17, until the distal portion of specimen retrieval instrument (10) is inserted into a patient as described above. Then, actuating rod (40) may be advanced distally relative to introducer tube (20) to expose retrieval bag (60) and hoop member (80) as shown in FIG. 16. Hoop member (80) may then resiliently expand to a substantially circular configuration, substantially elliptical configuration, or some other configuration (e.g., the configuration shown in FIGS. 2 and 4, etc.); and retrieval bag (60) may be unrolled and opened to receive a tissue specimen. By way of example only, retrieval bag (60) may be unrolled using a separate instrument (e.g., conventional tissue graspers, etc.), due to gravity, due to material properties of retrieval bag (60), due to expansion of one or more resilient members secured to or in retrieval bag (60), and/or by any other means. With retrieval bag (60) being unrolled and opened, a tissue specimen may be placed within retrieval bag (60); and retrieval bag (60) may be closed and removed from the patient as described herein or otherwise.

Figure 18:
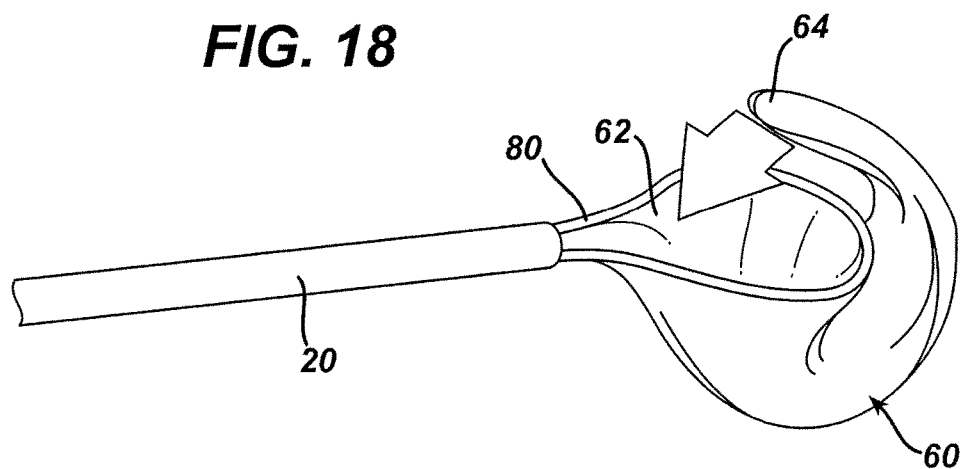
FIG. 18 is a perspective view of the distal end of an exemplary tissue retrieval device, with the closed end of a retrieval bag being inserted into the open end of the retrieval bag to initiate a rolling process.
Figure 19:
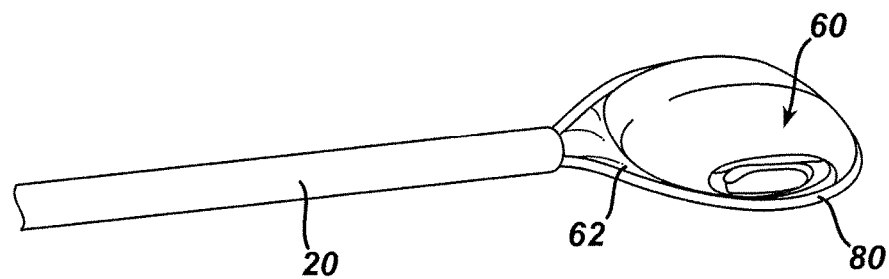
FIG. 19 is a perspective view of the distal end of the tissue retrieval device of FIG. 18, with the retrieval bag rolled into a resilient hoop.

FIGS. 18-19 depict a variation of the retrieval bag (60) rolling method shown in FIGS. 16-17. In this example, retrieval bag (60) is again rolled about an axis that is substantially transverse to the longitudinal axis defined by introducer tube (20). Unlike the process shown in FIGS. 16-17, though, the process shown in FIGS. 18-19 begins with closed bottom portion (64) of retrieval bag (60) being brought up and around the distal end of hoop member (80); and with closed bottom portion (64) then being tucked in open top portion (62) of retrieval bag (60) as shown in FIG. 18. Retrieval bag (60) is rolled in a proximal motion, until a substantial portion of rolled retrieval bag (60) is positioned within hoop member (80) as shown in FIG. 19. With retrieval bag (60) rolled into hoop member (80), retrieval bag (60) and hoop member (80) may be compressed within introducer tube (20). A tissue retrieval instrument (10) having a retrieval bag (60) with the configuration shown in FIGS. 18-19 may be used in the same way as a tissue retrieval instrument (10) having a retrieval bag (60) with the configuration shown in FIGS. 16-17. Examples of such uses are described above, while other suitable uses will be apparent to those of ordinary skill in the art in view of the teachings herein.

Figure 20:
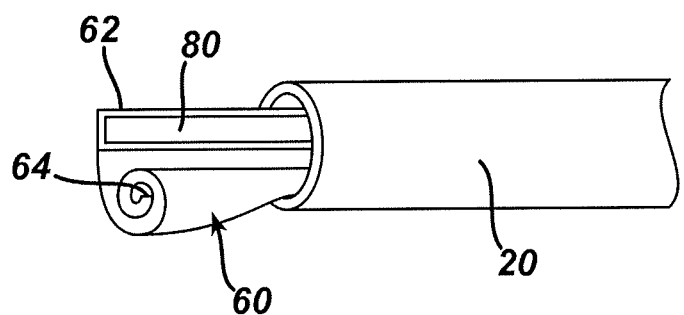
FIG. 20 is a perspective view of the distal end of an exemplary tissue retrieval device, with a resilient hoop and retrieval bag in a partially deployed position and with the retrieval bag in another exemplary rolled configuration.
Figure 21:
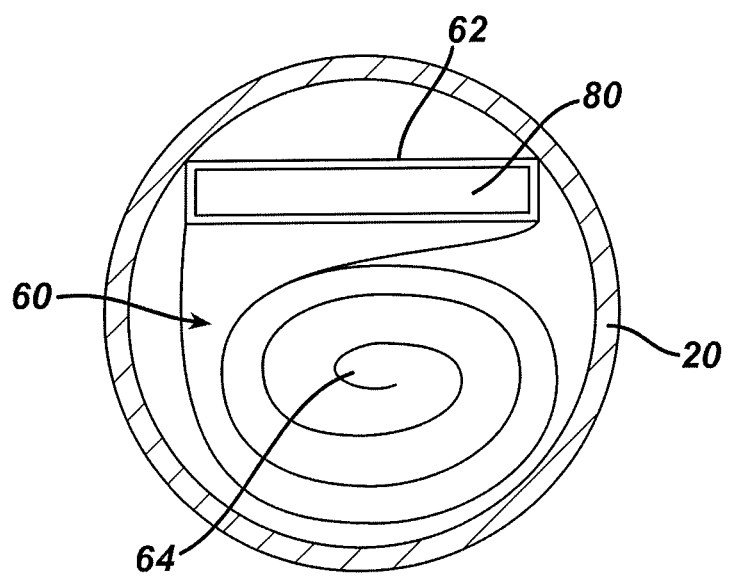
FIG. 21 is an end view of the tissue retrieval device of FIG. 20, with the resilient hoop and retrieval bag retracted within an introducer tube, and with the retrieval bag in the rolled configuration of FIG. 20.

FIGS. 20-21 depict yet another merely illustrative variation of a retrieval bag (60) rolling method. In this example, retrieval bag (60) is rolled about an axis that is substantially parallel to the longitudinal axis defined by introducer tube (20). This rolling process may be initiated by first moving closed bottom portion (64) laterally then starting with bottom portion (64) to roll retrieval bag (60) in an upward motion. This rolling may continue until rolled retrieval bag (60) is positioned just below hoop member (80) as shown in FIG. 21. With retrieval bag (60) rolled under hoop member (80), retrieval bag (60) and hoop member (80) may be compressed within introducer tube (20). While rolled retrieval bag (60) is positioned at the bottom of hoop member (80) in the present example, it should be understood that rolled retrieval bag (60) may alternatively be positioned at the top of hoop member (80).

In use, retrieval bag (60) may be positioned with hoop member (80) within introducer tube (20), as shown in FIG. 21, until the distal portion of specimen retrieval instrument (10) is inserted into a patient as described above. Then, actuating rod (40) may be advanced distally relative to introducer tube (20) to expose retrieval bag (60) and hoop member (80). FIG. 20 shows part of this process, where retrieval bag (60) and hoop member (80) are between being contained within introducer tube (20) and being exposed relative to introducer tube (20). When hoop member (80) is fully exposed, hoop member (80) may resiliently expand to a substantially circular configuration, substantially elliptical configuration, or some other configuration (e.g., the configuration shown in FIGS. 2 and 4, etc.); and retrieval bag (60) may be unrolled and opened to receive a tissue specimen. By way of example only, retrieval bag (60) may be unrolled using a separate instrument (e.g., conventional tissue graspers, etc.), due to gravity, due to material properties of retrieval bag (60), due to expansion of one or more resilient members secured to or in retrieval bag (60), and/or by any other means. With retrieval bag (60) being unrolled and opened, a tissue specimen may be placed within retrieval bag (60); and retrieval bag (60) may be closed and removed from the patient as described herein or otherwise.

While FIGS. 16-21 depict several merely illustrative ways in which a retrieval bag (60) may be rolled. It is contemplated that a retrieval bag (60) may be rolled in a variety of alternative ways. Various other suitable ways in which a retrieval bag (60) may be rolled will be apparent to those of ordinary skill in the art in view of the teachings herein. Furthermore, a retrieval bag (60) may be subject to various other processes (e.g., folding, wrapping, etc.) in addition to or in lieu of being rolled. Some examples of such other processes are described herein, while other examples of such other processes will be apparent to those of ordinary skill in the art in view of the teachings herein.

C. Exemplary Wrapping of Retrieval Bags

Figure 22:
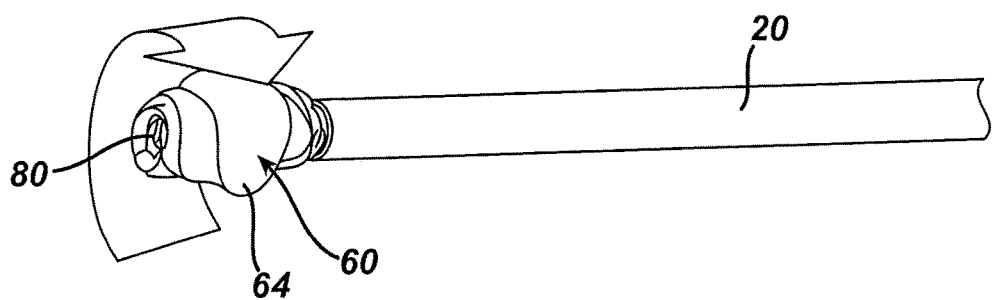
FIG. 22 is a perspective view of the distal end of an exemplary tissue retrieval device, with a retrieval bag in an exemplary wrapped configuration.

In addition to or in lieu of folding and/or rolling a retrieval bag (60) as part of a process of packing or otherwise loading the retrieval bag (60) within an introducer tube (60) or sheath (108), the retrieval bag (60) may be wrapped in a variety of ways. For instance, FIG. 22 shows an exemplary method whereby retrieval bag (60) is wrapped about hoop member (80). In other words, retrieval bag (60) is wrapped about a longitudinal axis defined by introducer tube (20), at the longitudinal position of hoop member (80). This wrapping process may be initiated by first moving closed bottom portion (64) laterally then up and over a side portion of hoop member (80), then over the top of hoop member (80) and down over the other side of hoop member (80), repeating the process until retrieval bag (60) is fully wrapped about hoop member (80). With retrieval bag (60) wrapped about hoop member (80), retrieval bag (60) and hoop member (80) may be compressed within introducer tube (20).

In use, retrieval bag (60) may be initially wrapped about hoop member (80) as shown in FIG. 22, with introducer tube (20) (not shown in FIG. 22) being distally positioned over hoop member (80) and retrieval bag (60) to compress and encompass hoop member (80) and retrieval bag (60). The distal portion of specimen retrieval instrument (10) is inserted into a patient as described above. Then, actuating rod (40) may be advanced distally relative to introducer tube (20) to expose retrieval bag (60) and hoop member (80) as shown in FIG. 22. Hoop member (80) may then resiliently expand to a substantially circular configuration, substantially elliptical configuration, or some other configuration (e.g., the configuration shown in FIGS. 2 and 4, etc.); and retrieval bag (60) may be unwrapped from hoop member (80) and opened to receive a tissue specimen. By way of example only, retrieval bag (60) may be unwrapped from hoop member (80) using a separate instrument (e.g., conventional tissue graspers, etc.), due to resilient expansion of hoop member (80), due to gravity, due to material properties of retrieval bag (60), due to expansion of one or more resilient members secured to or in retrieval bag (60), and/or by any other means. With retrieval bag (60) being unwrapped and opened, a tissue specimen may be placed within retrieval bag (60); and retrieval bag (60) may be closed and removed from the patient as described herein or otherwise.

Figure 23:
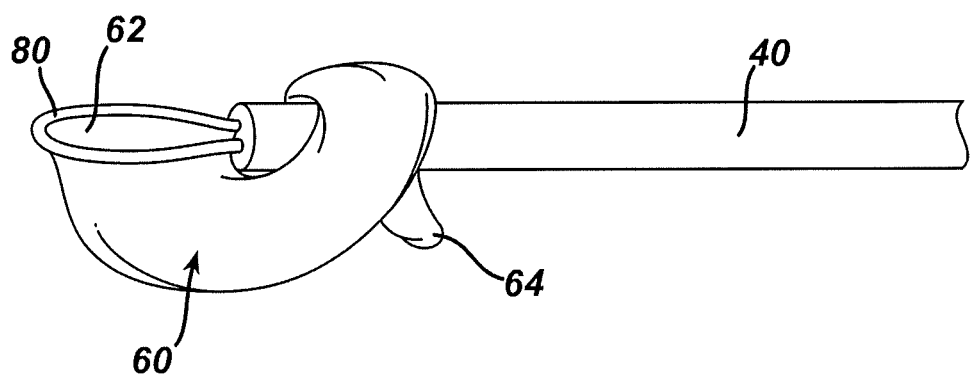
FIG. 23 is a perspective view of the distal end of an exemplary tissue retrieval device, with a retrieval bag in an initial stage of reaching another exemplary wrapped configuration.
Figure 24:
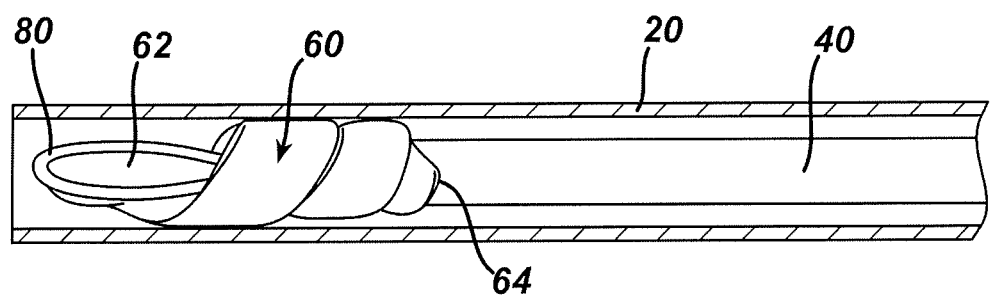
FIG. 24 is a perspective view of the distal end of the tissue retrieval device of FIG. 23, with the retrieval bag in another exemplary wrapped configuration.

FIGS. 23-24 depict another exemplary method of wrapping a retrieval bag (60). In this example, retrieval bag (60) is wrapped about actuating rod (40). In other words, retrieval bag (60) is wrapped about a longitudinal axis defined by introducer tube (20), at a longitudinal position that is proximal to hoop member (80). This wrapping process may be initiated by first moving closed bottom portion (64) laterally then up and over a side portion of actuating rod (40), then over the top of actuating rod (40) and down over the other side of actuating rod (40), repeating the process until retrieval bag (60) is fully wrapped about actuating rod (40). Initial stages of this process are shown in FIG. 23. With retrieval bag (60) wrapped about actuating rod (40), retrieval bag (60) and hoop member (80) may be compressed within introducer tube (20), as shown in FIG. 24. A tissue retrieval instrument (10) having a retrieval bag (60) with the configuration shown in FIGS. 23-24 may be used in the same way as a tissue retrieval instrument (10) having a retrieval bag (60) with the configuration shown in FIG. 22. Examples of such uses are described above, while other suitable uses will be apparent to those of ordinary skill in the art in view of the teachings herein.

FIGS. 25-27 depict another exemplary method of wrapping a retrieval bag (60). In this example, retrieval bag (60) is wrapped about itself. In particular, retrieval bag (60) is wrapped about a longitudinal axis defined by introducer tube (20), at a longitudinal position that is distal to hoop member (80). This wrapping process may be initiated by first moving closed bottom portion (64) to a position that is distal to hoop member (80), then twisting retrieval bag (60) while actuating rod (40) is held stationary and while retrieval bag (60) is kept in tension. With retrieval bag (60) twisted in front of actuating hoop member (80), hoop member (80) may be compressed within introducer tube (20) and twisted retrieval bag (60) may also be encompassed within introducer tube (20), as shown in FIG. 25 (which shows a distal portion of introducer tube (20) in cross-section).

In use, retrieval bag (60) may be positioned with hoop member (80) within introducer tube (20), as shown in FIG. 25, until the distal portion of specimen retrieval instrument (10) is inserted into a patient as described above. Then, actuating rod (40) may be advanced distally relative to introducer tube (20) to expose retrieval bag (60) and hoop member (80) as shown in FIG. 26. Hoop member (80) may then resiliently expand to a substantially circular configuration, substantially elliptical configuration, or some other configuration (e.g., the configuration shown in FIGS. 2 and 4, etc.); and retrieval bag (60) may be untwisted and opened to receive a tissue specimen. By way of example only, retrieval bag (60) may be untwisted using a separate instrument (e.g., conventional tissue graspers, etc.), due to gravity, due to material properties of retrieval bag (60), due to expansion of one or more resilient members secured to or in retrieval bag (60), and/or by any other means. With retrieval bag (60) being untwisted and opened as shown in FIG. 27, a tissue specimen may be placed within retrieval bag (60); and retrieval bag (60) may be closed and removed from the patient as described herein or otherwise.

While FIGS. 22-27 depict several merely illustrative ways in which a retrieval bag (60) may be wrapped. It is contemplated that a retrieval bag (60) may be wrapped in a variety of alternative ways. Various other suitable ways in which a retrieval bag (60) may be rolled wrapped will be apparent to those of ordinary skill in the art in view of the teachings herein. Furthermore, a retrieval bag (60) may be subject to various other processes (e.g., folding, rolling, etc.) in addition to or in lieu of being wrapped. Some examples of such other processes are described herein, while other examples of such other processes will be apparent to those of ordinary skill in the art in view of the teachings herein.

III. Exemplary Capsule for Retrieval Bag

FIGS. 28-29 depict an exemplary capsule (2000) that may be used to contain retrieval bag (60) and/or hoop member (80) before and during insertion of the distal end of a specimen retrieval device in a patient. In particular, FIG. 28 shows capsule (2000) positioned at the distal end of introducer tube (20), encompassing and containing hoop member (80). While retrieval bag (60) is not shown in FIG. 28, it should be understood that capsule (2000) may further encompass and contain retrieval bag (60) in addition to encompassing and containing hoop member (80). By way of example only, retrieval bag (60) may be folded, rolled, and/or wrapped in accordance with the teachings above in order to be contained within capsule (2000). In addition or in the alternative, retrieval bag (60) may be wadded, stuffed, and/or otherwise configured in order to be contained within capsule (2000). While capsule (2000) encompasses and contains both hoop member (80) and retrieval bag (60) in the present example, it should be understood that capsule (2000) may alternatively encompass and contain just part of hoop member (80) and/or just part of retrieval bag (60).

In containing hoop member (80) and retrieval bag (60), capsule (2000) of the present example is configured to resist the outward resilient bias of hoop member (80). Capsule (2000) is thus configured to perform a containment function similar to that described above with respect to introducer tube (20) and sheath (108). In view of this, it should be understood that hoop member (80) need not necessarily be secured to an actuating rod (40) that is translatable within introducer tube (20) in versions of a specimen retrieval device that include capsule (2000). In other words, the longitudinal position of hoop member (80) relative to introducer tube (20) may be substantially fixed in some such versions. Similarly, it should be understood that a retractable sheath (108) is not necessarily required in versions of a specimen retrieval device that include capsule (2000). Of course, some versions of a specimen retrieval device that include capsule (2000) may nevertheless include a translatable actuating rod (40) and/or retractable sheath (108). For instance, capsule (2000) may be selectively contained within or exposed relative to an introducer tube (20) or sheath (108).

Capsule (2000) of the present example is formed of an environmentally responsive material. In particular, capsule (2000) is configured to degrade or otherwise break apart when capsule (2000) is exposed to environmental conditions associated with the interior of a patient's body. For instance, capsule (2000) may degrade or break apart when capsule (2000) is exposed to at least a certain amount of carbon dioxide (e.g., which may be associated with an artificially insufflated abdomen of a patient, etc.), temperatures exceeding a threshold, the presence of one or more bodily fluids, etc. Other suitable environmental conditions associated with the interior of a patient's body that capsule (2000) may respond to will be apparent to those of ordinary skill in the art in view of the teachings herein. To provide such environmental responsiveness, capsule (2000) may be formed of polylactic acid (PLA), polyglycolic acid (PGA), PLA/PGA, a variety of polymerized hydrogels, and/or any other suitable material or combination of materials. Other various materials that may be used to form capsule (2000) will be apparent to those of ordinary skill in the art in view of the teachings herein. Capsule (2000) may also include perforations or other structural features that may assist in degradation or breaking apart of capsule (2000) when capsule (2000) is introduced to the interior of the patient's body. When capsule (2000) degrades or breaks apart in a manner sufficient to expose hoop member (80) and retrieval bag (60), any remaining fragments of capsule (2000) may continue to degrade within and/or be absorbed by the patient's body.

The proximal end of capsule (2000) may be secured to the distal end of introducer tube (20) in any suitable fashion. For instance, an adhesive may be used to secure capsule (2000) to the distal end of introducer tube (20). As another merely illustrative example, a portion of the proximal end of capsule (2000) may overlap a portion of the distal end of introducer tube (20), such that an interference fit or friction may substantially secure capsule (2000) to introducer tube (20) before the specimen retrieval instrument is used in a surgical procedure. In addition or in the alternative, the resilient bias of hoop member (80) may cause hoop member (80) and/or retrieval bag (60) to bear against the interior of capsule (2000), which may substantially secure capsule (2000) relative to introducer tube (20). Still other suitable ways in which capsule (2000) may be substantially secured relative to introducer tube (20) will be apparent to those of ordinary skill in the art in view of the teachings herein.

In use, capsule (2000) may be substantially secured relative to introducer tube (20), hoop member (80), and retrieval bag (60), as shown in FIG. 28, until the distal portion of the specimen retrieval instrument is inserted into a patient as described above. With the distal portion of the specimen retrieval instrument being inserted into a patient, capsule (2000) is exposed to environmental conditions associated with the interior of the patient's body. Being so exposed, capsule (2000) breaks apart as shown in FIG. 29 to reveal hoop member (80) and retrieval bag (60). Hoop member (80) may then resiliently expand to a substantially circular configuration, substantially elliptical configuration, or some other configuration (e.g., the configuration shown in FIGS. 2 and 4, etc.); and retrieval bag (60) may be unfurled and opened to receive a tissue specimen. By way of example only, retrieval bag (60) may be unfurled using a separate instrument (e.g., conventional tissue graspers, etc.), due to gravity, due to material properties of retrieval bag (60), due to expansion of one or more resilient members secured to or in retrieval bag (60), and/or by any other means. With retrieval bag (60) being unfurled and opened, a tissue specimen may be placed within retrieval bag (60); and retrieval bag (60) may be closed and removed from the patient as described herein or otherwise.

In some other versions, capsule (2000) is not formed of a material that is biodegradable, bioabsorbable, or otherwise responsive to one or more environmental conditions within a patient's body. For instance, capsule (2000) may instead be formed of a conventional metal or plastic, etc. In some such versions, capsule (2000) may simply be pulled off of hoop member (80) and retrieval bag (60) (e.g., using conventional tissue graspers, etc.) once the distal end of the specimen retrieval instrument has been sufficiently inserted in a patient. A surgeon may then simply place removed capsule (2000) in the open retrieval bag (60) for subsequent removal; or may do anything else with removed capsule (2000) as desired.

While capsule (2000) is shown as having a closed distal end, it should be understood that capsule (2000) may instead have an open distal end or any other suitable configuration.

As noted above, capsule (2000) may be used in conjunction with any of the methods of loading/packing retrieval bag (60) described herein. It should also be understood that capsule (2000) may be readily incorporated into any of the tissue retrieval devices described in any of the patents or patent applications cited herein. Various suitable ways in which capsule (2000) may be incorporated into any of the tissue retrieval devices described in any of the patents or patent applications cited herein will be apparent to those of ordinary skill in the art.

IV. Other

As noted above, the various versions of tissue retrieval devices described herein, including but not limited to the various versions of retrieval bags described herein, may be used in a conventional endoscopic procedure that includes the insertion of the introducer tube or other component through a small opening, e.g., an incision, natural orifice, or trocar access port. Of course, tissue retrieval devices may be used in conjunction with any other suitable surgical or medical procedure, such as endoscopic/laparoscopic procedures, open surgical procedures, or robotic-assisted surgery, etc. Still other various settings and combinations in which a tissue retrieval device or tissue retrieval bags may be used will be apparent to those of ordinary skill in the art in view of the teachings herein.

While several retrieval bags and deployment mechanisms have been discussed in detail above, it should be understood that the components, features, configurations, and methods of using the bags and deployment mechanisms discussed are not limited to the contexts provided above. In particular, components, features, configurations, and methods of use described in the context of one of the retrieval bags may be incorporated into any of the other retrieval bags. One merely exemplary additional feature that may be provided in any of the retrieval bags described herein is one or more weld lines. Such weld lines may be intermittent or continuous along the length of the bag. Such weld lines, offering alternating areas of stiffness along the surface of the bag, may enhance the closure of a bag due to the tendency of areas of lesser stiffness to buckle, deform, or fold. In this way, a retrieval bag may be forced or encouraged to buckle or fold in a desired manner as the bag is closed. Still other additional and alternative suitable components, features, configurations, and methods of using the above-described retrieval devices will be apparent to those of ordinary skill in the art in view of the teachings herein.

While several tissue retrieval instruments and components thereof have been discussed in detail above, it should be understood that the components, features, configurations, and methods of using the tissue retrieval instruments discussed are not limited to the contexts provided above. In particular, components, features, configurations, and methods of use described in the context of one of the tissue retrieval instruments may be incorporated into any of the other tissue retrieval instruments. One merely exemplary additional feature that may be provided in any of the tissue retrieval instruments described herein includes retrieval bags having various sizes and geometries. For example, some tissue retrieval instruments may be designed with small, medium, or large retrieval bags. Also for example, some tissue retrieval instruments may use retrieval bags having pleats and/or gussets that allow for expansion when holding larger specimens. It should also be understood that any of the tissue retrieval instruments and tissue retrieval bags described herein may be capable of receiving tissue specimens and removing tissue specimens from a patient without such tissue specimens needing to be morcellated or otherwise reduced in size before being received and removed by the tissue retrieval instrument and bag. Still other additional and alternative suitable components, features, configurations, and methods of using the tissue retrieval instruments will be apparent to those of ordinary skill in the art in view of the teachings herein.

While the tissue retrieval instruments of the above-described examples are actuated manually by advancing a thumb ring distally relative to finger rings, by manually retracting a sheath, or in some other manual fashion, it should be understood that any of the tissue retrieval instruments described herein may instead be actuated in any other suitable fashion. By way of example only, a tissue retrieval instrument may instead be actuated electromechanically (e.g., using one or more electrical motors, solenoids, etc.), pneumatically, and/or hydraulically. Various suitable ways in which such alternative forms of actuation may be provided in a tissue retrieval instrument will be apparent to those of ordinary skill in the art in view of the teachings herein. Similarly, various other suitable ways in which a tissue retrieval instrument may be actuated will be apparent to those of ordinary skill in the art in view of the teachings herein.

It should be understood that any of the retrieval bags described herein may have various types of construction. By way of example only, any of the retrieval bags described herein may be constructed from at least one layer of an elastomeric or polymeric material such as but not limited to polyurethane, polyethylene, polypropelene, polyester (Duralar), Poly-isoprene, silicone, vinyl, or a polytetrafluroethyelene (Teflon®). For example, any retrieval bag described herein may comprise a single layer of elastomeric or polymeric material. Alternatively, any retrieval bag described herein may be formed of two or more layers of material. For instance, two or more layers of a retrieval bag wall may be aligned and joined together by adhesives, heat welding, heat staking, RF welding, ultrasonically welding, or other suitable method of attachment. Any retrieval bag described herein may also be cut at an angle to provide a taper or special shapes suitable for specific organs of body (e.g., tissue shapes, etc.), which may facilitate removal of the retrieval bag from a patient. Furthermore, any retrieval bag described herein may incorporate flexible metal meshes, thermoformed plastic meshes, fabrics, or aramid fibers such as Kevlar® for reinforcement. Still other suitable materials that may be used to form retrieval bags as described herein, including combinations of materials, will be apparent to those of ordinary skill in the art in view of the teachings herein. Similarly, various other suitable compositions of the walls of the retrieval bags described herein, including but not limited to various structures, components, and features that may be incorporated into the walls of the retrieval bags described herein, will be apparent to those of ordinary skill in the art in view of the teachings herein.

In any of the above described tissue retrieval instruments, the tissue retrieval bag may include a fold-over flap (not shown) for closing the bag. For instance, such a fold-over flap may be used instead of (or in addition to) using a string to effect closure of the bag. Such a fold-over flap may include an adhesive (e.g., pressure sensitive adhesive, etc.) that substantially keeps the flap in a closed position after the flap has been moved to a closed position. A peel-away strip or similar feature may be used to cover such an adhesive before the flap is closed. A conventional grasping instrument or other type of device may be used to peel the peel-away strip and/or close the flap over the mouth of the bag while the bag is still inside the patient. In some other variations, a tissue retrieval bag may be formed at least in part of a material that provides significant static adhesion or other type of adhesion to itself. For instance, the interior surfaces of the tissue retrieval bag may be configured to adhere to each other and/or to adhere to tissue/objects placed in the bag, to reduce the likelihood of tissue/objects in the bag falling out of the bag. In some such versions, a closure string is omitted. Other suitable variations of a tissue retrieval bag will be apparent to those of ordinary skill in the art in view of the teachings herein.

Versions of the present invention have application in conventional endoscopic and open surgical instrumentation as well as application in robotic-assisted surgery.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

The invention claimed is:

1. A method of loading a retrieval bag within a specimen retrieval instrument, wherein the specimen retrieval instrument comprises a tubular member, a rod positioned within the tubular member, an expandable member, and a retrieval bag, wherein the tubular member has a distal end and a proximal end, wherein the tubular member defines a central longitudinal axis, wherein the retrieval bag is secured to the expandable member, wherein the tubular member is configured to contain the expandable member and the retrieval bag, wherein the tubular member is configured to hold the expandable member in a compressed state to contain the expandable member, wherein the expandable member is configured to open the retrieval bag when the expandable member is expanded to an expanded state, wherein the rod comprises a distal end and a proximal end, wherein the expandable member is located at the distal end of the rod, the method comprising:
  (a) reducing the size of the retrieval bag to create a packed retrieval bag, wherein the act of reducing the size of the retrieval bag comprises bending the expandable member about a second axis to position a distal portion of the expandable member proximally in relation to the distal end of the rod and wrapping the retrieval bag about one or both of the rod and the expandable member; and
  (b) positioning the packed retrieval bag and the expandable member within the tubular member, wherein the expandable member is in a compressed state within the tubular member, wherein the expandable member extends along the central longitudinal axis of the tubular member.

2. The method of claim 1, wherein the retrieval bag comprises an open end secured to the expandable member.

3. The method of claim 2, wherein the retrieval bag comprises a closed bottom end.

4. The method of claim 1, wherein the act of bending the expandable member about the second axis results in the distal portion of the expandable member being positioned above a top potion of the rod, wherein the act of wrapping the retrieval bag around the expandable member results in the closed end of the retrieval bag being positioned below a bottom portion of the rod.

5. The method of claim 4, wherein the expandable member has a top portion, wherein the top portion of the expandable member faces the rod after the expandable member is bent about the second axis.

6. The method of claim 4, wherein the expandable member has a bottom portion, wherein the bottom portion faces the rod after the expandable member is bent about the second axis.

7. The method of claim 4, wherein the retrieval bag prevents the expandable member from touching the rod.

8. The method of claim 4, wherein the retrieval bag is in contact with at least one point of the tubular member.

9. The method of claim 4, wherein the bent portion of the expandable member is in contact with at least one point of the rod after the expandable member is bent about the second axis.

10. The method of claim 4, wherein the second axis is perpendicular to the first longitudinal axis.

11. The method of claim 1, wherein the expandable member has a hoop configuration.

12. A method of loading a retrieval bag within a specimen retrieval instrument, the method comprising:
  (a) providing a specimen retrieval instrument, wherein the specimen retrieval instrument comprises:
    (i) a tubular member defining a central longitudinal axis,
    (ii) a rod comprising a distal end, wherein the rod is located within the tubular member,
    (iii) an expandable member extending distally from the rod, and
    (iv) a retrieval bag, wherein the retrieval bag has an open top end secured to the expandable member and a closed bottom end, wherein the tubular member is configured to contain the expandable member and the retrieval bag, wherein the tubular member is configured to hold the expandable member in a compressed state to contain the expandable member, wherein the expandable member is configured to open the retrieval bag when the expandable member is expanded to an expanded state;
  (b) bending the expandable member to position the distal end of the expandable member proximal to the distal end of the rod;
  (c) packing the retrieval bag, wherein the act of packing the retrieval bag comprises wrapping at least a portion of the retrieval bag around the expandable member and; and
  (d) positioning the packed retrieval bag and the expandable member within the tubular member, wherein the expandable member extends along the central longitudinal axis, wherein the act of positioning the packed retrieval bag and the expandable member within the tubular member further comprises compressing the expandable member.

13. The method of claim 12, wherein the retrieval bag is twisted prior to wrapping the retrieval bag around the rod.

14. The method of claim 12, wherein the closed bottom end of the retrieval bag is positioned distal from the open top end when the portion of the retrieval bag is wrapped around the rod.

15. The method of claim 12, wherein the retrieval bag is unwrapped from around the rod in response to expansion of the expandable member.

16. The method of claim 12, wherein the retrieval bag is wrapped around a third axis.

17. A method of loading a retrieval bag within a specimen retrieval instrument, wherein the specimen retrieval instrument comprises a tubular member having a central longitudinal axis, an expandable member, a rod within the tubular member, and a retrieval bag, wherein the expandable member is distal in relation to the rod, wherein the retrieval bag comprises an open end secured to the expandable member and a closed end, wherein the tubular member is configured to contain the expandable member and the retrieval bag, wherein the tubular member is configured to hold the expandable member in a compressed state to contain the expandable member, wherein the expandable member is configured to open the retrieval bag when the expandable member is expanded to an expanded state, the method comprising:
  (a) reducing the size of the retrieval bag to create a packed retrieval bag, wherein the act of reducing the size of the retrieval bag comprises:
    (i) bending the expandable member to position the distal end of the expandable member proximal to the distal end of the rod, and
    (ii) wrapping at least a portion of the retrieval bag around one or both of the expandable member and the rod such that the closed end of the retrieval bag is proximal in relation to the distal end of the rod yet on the opposite side of the rod as the expandable member; and (b) positioning the packed retrieval bag and the expandable member within the tubular member, wherein the expandable member is in a compressed state within the tubular member, wherein the expandable member extends along the central longitudinal axis of the tubular member.

18. The method of claim 17, wherein the retrieval bag is twisted prior to wrapping.

19. The method of claim 17, wherein the expandable member is bent around a second axis, and wherein the second axis is perpendicular to the central longitudinal axis.

20. The method of claim 19, wherein the retrieval bag is bent around a third axis, wherein the second axis and the third axis are parallel to each other.

* * * * *